US008122550B2

(12) United States Patent
Johnson

(10) Patent No.: US 8,122,550 B2
(45) Date of Patent: Feb. 28, 2012

(54) METHOD OF TREATING OSTEOARTHRITIS USING INSOLES

(76) Inventor: Lanny L. Johnson, Okemos, MI (US)

( * ) Notice: Subject to any disclaimer, the term of this patent is extended or adjusted under 35 U.S.C. 154(b) by 0 days.

(21) Appl. No.: 12/603,160

(22) Filed: Oct. 21, 2009

(65) Prior Publication Data

US 2010/0192418 A1 Aug. 5, 2010

Related U.S. Application Data

(60) Provisional application No. 61/107,604, filed on Oct. 22, 2008.

(51) Int. Cl.
*A43B 7/18* (2006.01)
*A61F 5/14* (2006.01)

(52) U.S. Cl. .................... 12/146 M; 12/142 N; 602/66; 36/144; 36/43

(58) Field of Classification Search .................... 36/144, 36/127, 43, 44, 142, 143; 602/62, 66; 12/142 N, 12/146 M
See application file for complete search history.

(56) References Cited

U.S. PATENT DOCUMENTS

| | | | | |
|---|---|---|---|---|
| 4,862,605 | A * | 9/1989 | Gardner et al. | 36/43 |
| 5,579,591 | A * | 12/1996 | Kousaka et al. | 36/31 |
| 6,725,578 | B2 * | 4/2004 | Kerrigan | 36/144 |
| 7,373,740 | B2 | 5/2008 | Lo | |
| 7,475,498 | B2 | 1/2009 | Litchfield et al. | |
| 7,484,318 | B2 | 2/2009 | Finkelstein | |
| 7,484,319 | B2 | 2/2009 | Cheskin et al. | |
| 2001/0047146 | A1 * | 11/2001 | Toda | 602/62 |
| 2010/0154252 | A1 * | 6/2010 | Avent et al. | 36/91 |

OTHER PUBLICATIONS

Treatment of Osteoarthritis of the Knee (Non-Arthroplasty)—Clinical Practice Guideline, American Academy of Orthopaedic Surgeons, Dec. 6, 2008, pp. i-vi and 31-37.

* cited by examiner

*Primary Examiner* — Ted Kavanaugh
(74) *Attorney, Agent, or Firm* — David J. Dawsey; Michael J. Gallagher; Gallagher & Dawsey Co., LPA

(57) ABSTRACT

The present invention provides devices, methods, and kits for reducing joint pain and treating conditions of weight-bearing joints. The methods are accomplished through the use of a cushioned wedged insole or slab that selectively reduces pressure by cushioning impact and redistributing forces away from affected joints or joint compartments. Further, insoles are provided, which mimic the combination of fatty globules and the surrounding restricting fibrous network cushioning structures found in the foot.

11 Claims, 19 Drawing Sheets

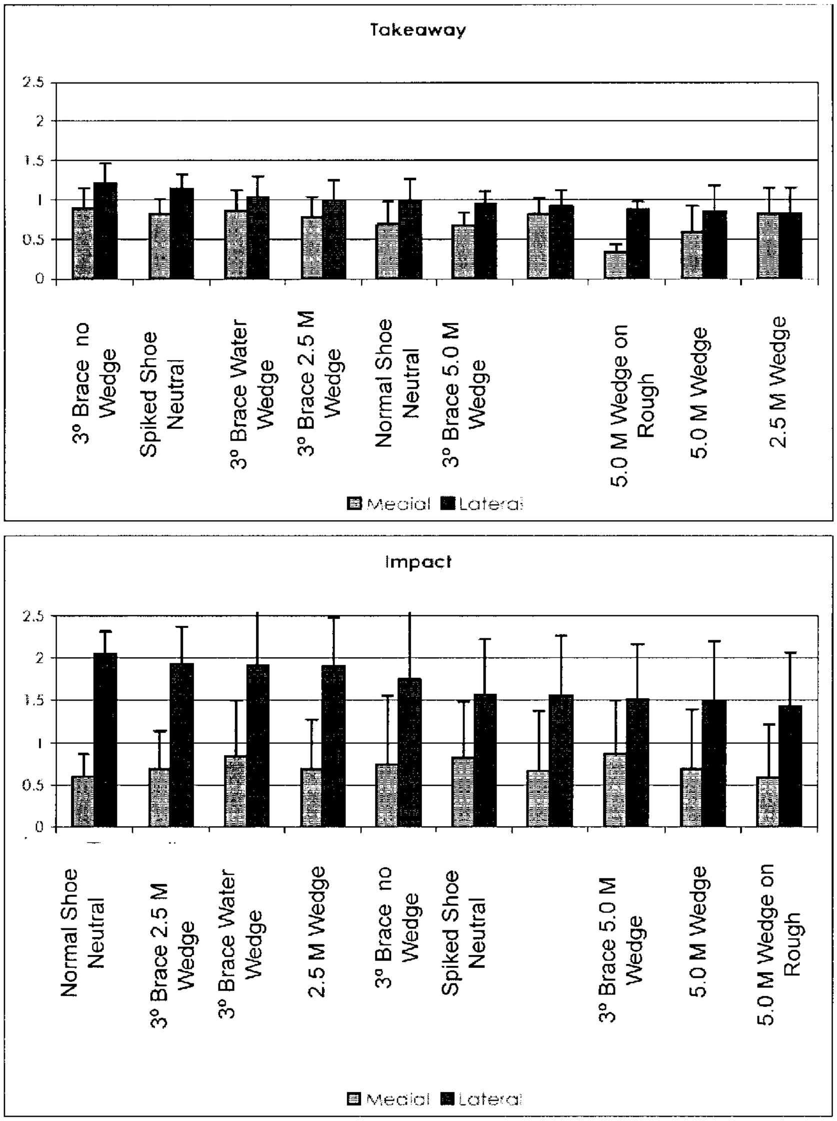
FIG. 9A-B

ML Forces and Alignment

| | DM | SC | PS | |
|---|---|---|---|---|
| Alignment | 11° Valgus | 0° | 5° Varus | |
| Flexion Contracture | 15° | 5° | 0° | |
| Lateral Forces | 54% | 29% | 41% | (during normal gait) |
| Medial Forces | 46% | 71% | 59% | (during normal gait) |

METHOD OF TREATING OSTEOARTHRITIS USING INSOLES

CROSS-REFERENCE TO RELATED APPLICATIONS

This application claims benefit of priority to U.S. patent application Ser. No. 61/107,604 filed on Oct. 22, 2008, the contents of which are herein incorporated by reference in their entirety.

FIELD OF THE INVENTION

The present invention relates generally to the field of orthotics, and particularly to insoles for the treatment, prevention, and rehabilitation of injury and medical conditions associated with weight-bearing joints.

BACKGROUND OF THE INVENTION

The human leg is a complex mechanism, absorbing and dissipating the impact forces generated by supporting and moving the body. There are high impact axial loads with acceleration and deceleration even in activities of daily living. For instance when standing one half body weight goes through each knee. While walking two and one half body weight goes through each knee with each step as the person slightly sways side to side. Getting out of a chair without help of the arms increases the axial forces across the knee almost twice body weight. Damage may occur with work or activities of daily living.

High impact sports, such as running and tennis are known to significantly increase loads on weight-bearing joints. As such, sports injuries commonly involve damage to the knees, ankles and hips. Even sports previously considered low impact can generate significant loads on weight-bearing joints. For example, golf is considered by many to be low impact sport; however, the golf swing at ball impact typically generates loads of about 3.5 to 4.5 times the golfer's weight on the knees. Interestingly these loads are simultaneously transmitted to both knees at impact. These increased loads are generated from the impact of the club having a long lever arm hitting a ball while the player's muscles are contracting to secure footing or fixation to the ground. Thus, even those that actively participate in sports such as golf are susceptible to injury of weight-bearing joints.

Even minor imbalances in the foot that are not harmful or even detectable under usual circumstances can make one more vulnerable to injury. Imbalances my result in the body compensating or overcompensating in an attempt to equalize balance. Such compensation or overcompensation may result in fatigue, which is known to increase risk of injury. In addition proper imbalance may reduce the efficiency of muscle development and may decrease the body's mechanical efficiency when participating in sports or other activities.

Risk of damage to the body is not limited to those that participate in sports. A variety of adverse knee, ankle, foot and hip medical conditions are prevalent among the general population and in particular among the aging population. In fact, as the world's population ages, these conditions will become more widespread—while only 1 out of every 20 people was age 65 or older in 1950, by 2050 that number will increase to 1 out of 6.

Scientists have recently established a link between a protein that declines with age and the development of osteoarthritis (OA), a common disease of aging affecting nearly 27 million Americans.[1] Specifically, the loss of the protein (HMGB2; found in the surface layer of joint cartilage) leads to the progressive deterioration of the cartilage—the hallmark of OA. Cartilage is the tissue layer that sustains joint loading (weight bearing) and allows motion at joint surfaces. Whereas normal cartilage provides a durable, low-friction, load-bearing surface, damaged cartilage significantly reduces mobility. Currently, no effective treatment for this degenerative disease exists, apart from palliative drugs for pain and inflammation.

OA typically begins with a disruption of the surface layer of cartilage, called the superficial zone. Functionally, of the four layers of cartilage present in joints, this is the most important. In non-diseased joints the cartilage surface is smooth, enabling joint surfaces to interact without friction. However, the cartilage of the superficial zone begins to deteriorate as OA progresses triggering an irreversible process that eventually leads to the loss of underlying layers of cartilage. The fragments of cartilage are dispersed in the joint causing reaction of the joint lining, inflammation and the symptoms of pain and swelling. Over time, bone surfaces begin to grind painfully against one another.

The knee is the most common lower limb site for OA, with the disease affecting the tibiofemoral and patellofemoral joints either in isolation or combination, with the medial tibiofemoral compartment as the most commonly affected.[2] Patients with knee OA report knee pain and difficulty with walking, stair-climbing and housekeeping.[3]

Management strategies for knee OA can be regarded as primary (reducing risk factors to lessen disease incidence); secondary (intervening to slow or prevent progression to serious disease); or tertiary (treating pain and disability).[4] To date, most knee OA research has focused on tertiary strategies relating to pain management. Among these strategies, the primary emphasis has been on drug therapies, which typically include unwanted side effects and can be costly.[5]

Currently, no cure exists for OA, and joint replacement is the only established treatment for end-stage OA. In the case of the knee, the cost for such an operation is high an estimated $35,000 for those without health insurance. The operation also typically entails a 3-7 day hospital stay. During the surgery the doctor assesses the condition of the joint surfaces, removing damaged bone and cartilage, and implanting new joint surfaces made of plastic and metal. These new joint surfaces are not permanent, and will likely need to be replaced after 10 to 15 years. Thus, slowing the disease's progression is essential to reducing its impact both personally and upon society, as a slower disease progression rate would, for many patients, eliminate the need for the joint replacement procedure entirely.

As if OA itself were not troubling enough, a recent study published in BioMed Central's open access journal, *Arthritis Research & Therapy*, found that increased waist circumference and body mass index (BMI) were associated with the risk of both knee and hip joint replacement. Further, in addition to the increased joint loading caused by the excess baggage accumulating around the world's waistlines, the adipose tissue itself can release cytokines that have been implicated in joint damage.[6] Cytokines can act to accelerate progression of OA by contributing to the deterioration of cartilage and hastening the onset of bone/bone contact.

Gel and cushioned insoles as well as heel wedges and unloader braces have been proposed to decrease knee, ankle and foot pain by unloading forces on the joint. However, most insoles act merely to alleviate pain while doing little to treat the injury or to prevent progression of OA. Specifically, they are a component of tertiary management strategies designed to manage pain. However, studies find that while insoles may provide some cushion or softening, they often do not provide continual support. For instance, cushion insoles tend to bottom out or lose their contour when under load or increased load. As such, the cushion may provide some comfort but may not reduce peak axial load on the joint. In fact the gel type insoles may actually increase the peak axial load because the foot at impact rapidly compresses the material on way to impact rather than modulating or absorbing the person's weight. Further, while heel wedges have been proposed to unload the joint, not all experts support the use of these insoles to help patients suffering from arthritis. For example, in the case of symptomatic medial compartmental OA of the knee, the official stance of the American Academy of Orthopedic Surgeons (AAOS) is to refrain from prescribing lateral heel wedges, as their systematic review of the wedges provided no "evidence that lateral heel wedges are more effective than neutral heel wedges, when assessed with the WOMAC instrument for up to 24 months." The AAOS' "Full Guideline" for treatment of osteoarthritis of the knee (Dec. 6, 2008) went on to state "[These data suggest that there is no benefit to using lateral heel wedges, and there is the possibility that those who do not use them may experience fewer OA of the knee symptoms." Thus, conventional insoles and heel wedges, including lateral heel wedges have not been deemed effective as an OA treatment. In addition, this report goes on by stating while unloader braces have also been proposed there is no clear evidence in the literature of their effectiveness.

While developing primary management strategies for OA could be difficult, especially given its link to aging and decreasing levels of certain molecules, secondary strategies, including those designed to slow the progression of the disease, could be extremely helpful. Further, with increased interest in sports and increased lifespan, there exist a need to develop new noninvasive devices and methods for the prevention and treatment of injuries and medical conditions related to weight-bearing joints, including the knee, ankle, foot and hip.

SUMMARY OF THE INVENTION

The present invention address the need to provide noninvasive devices and methods to prevent, treat or rehabilitate injuries and medical conditions associated with weight-bearing joints and provides related benefits. The devices and methods provided herein may be used to treat or prevent conditions associated with the knee, ankle, foot, hip, spine and the like. These objects are accomplished by providing devices and methods that incorporate insoles having desired properties which shift, dissipate, or affect forces displaced on the joints, such as mediolateral or axial forces. The devices and methods provide insoles which absorb impact and effectively disperse forces without bottoming out. Further, the devices are constructed from memory materials that reform in short intervals between steps or moments of unloading.

In one aspect of the present invention a cushioned wedged slab constructed from a viscoelastic material is provided, which includes a flat bottom and a sloping top that defines a lower edge and an upper edge. The cushioned wedged slab partially collapses under compressive forces and rebounds when the compressive forces are removed. The cushioned wedged slab retains a wedged configuration throughout its partial collapse. In preferred embodiments the viscoelastic material is EVA foam or modification thereof, such as with ENGAGE. EVA foam provides a plurality of encapsulated gas pockets in the form of closed cells, which when surrounded by the EVA can mimic fatty globules surrounded by fibrous tissue found in the foot. As such, it has been found that EVA foam can be used to mimic the natural anatomical protective structures of the foot. There is a soft thin material covering the surface for comfort and security. In some embodiments the cushioned wedged slab is provided for the construction of a cushioned wedged insole, such as a lateral wedged insole or a medial wedged insole. In other embodiments, the cushioned wedged slab is used in the construction of a heel wedge or a wedge for the metatarsals or ball of the foot. Preferably the wedged slab is cut to about 4.25 inches wide by about 14 inches in length.

In preferred embodiments a cushioned wedged insole is provided, which includes the cushioned wedged slab shaped for insertion into footwear such as a shoe, boot, slipper and the like. In some embodiments, the cushioned wedged insole is used with an athletic shoe, such as a golf shoe, a tennis shoe, ski boot or a cleated shoe.

The cushioned wedged insole may be a lateral wedged insole, which is characterized by the upper, higher or thicker edge of the wedged insole positioned along its outer length and the lower edge of the wedged insole positioned along its inner length. In other embodiments, the cushioned wedged insole is a medial wedged insole, which is characterized by the upper, higher or thicker edge of the wedged insole positioned along its inner length and the lower edge of the wedged insole positioned along its outer length. By providing lateral and medial wedged insoles forces are selectively redirected from medial and lateral chambers of the knee, ankle or foot. In preferred embodiments the cushioned wedged insole is tailored to extend from the subject's heel to the metatarsal heads. In some embodiments the length of the wedged insole is from about 3.5 inches to about 12 inches. Preferably the cushioned wedged insole or slab measures up about 4.25 inches in width and about 14 inches long to accommodate the size of most feet and may be further cut to the needs of the user.

The upper and lower edges of the cushioned wedged insole or slab may be provided such that their difference is sufficient to control pronation of the foot and ankle during a type of activity for which the insole is used. Although the thickness may vary according to the construction material, particular benefit when using EVA is shown when the upper edge is from about 7 mm to about 14 mm and has a slope from about 2.5 to about 5 degrees. In preferred embodiments, the slope is less than about 10 degrees. In some embodiments, the thickness of the upper edge measures about 12 millimeters, the thickness of the lower edge measures about 4 millimeters and the slope is about 5 degrees. In other embodiments, the thickness of the upper edge measures about 7 millimeters, the thickness of the lower edge measures about 4 millimeters and the slope is about 2.5 degrees. In some embodiments, the upper edge compresses to about 5 millimeters under 25 ft. lbs. of focal compressive force. In certain embodiments the wedged insole can be chambered or a series of layers including chambers.

The cushion wedged insole material is such that it mimics the human anatomy of the foot pad. The human foot pad is composed of many chambers of fat surrounded by a network of tough fibrous tissue. The compression of the fat globule absorbs the impact but is restricted from bottoming out by the surrounding tough network of fibrous tissue. EVA or a modification thereof replicates the anatomy by the closed cell foam nature and the resilience of the elastomer. For example, closed cell foams such as EVA that encapsulate pockets of air or gas can be used to mimic the fatty globules in the foot, and surrounding material like EVA can be used to mimic the fibrous tissue which prevents collapse of the fatty globules in the foot. Another variation mimicking the anatomy of a foot occurs by incorporating capsules of soft fatty simulated materials corresponding to fatty chambers of the foot pad, surrounded by more rigid materials simulating the fibrous tissue. Preferably, both rigid and soft materials are provided as solids. This later arrangement may be provided as a multilayered configuration.

In another aspect of the invention a method of reducing forces from the medial compartment of the knee or ankle of a subject during an exercise or gait is provided, the method including use of a lateral wedged insole such that that the upper edge of the wedged insole follows an outer or lateral length of the shoe. In other embodiments a method of reducing pressure from the lateral knee or ankle compartment of a subject is provided, the method including use of a medial wedged insole in a shoe of the subject such that the upper edge of the wedged insole follows an inner length or medial length of the shoe. In each embodiment, preferably the insole extends from about the heel to about the metatarsals of the subject.

In other aspect of the present invention a method of reducing forces on an arthritic joint is provided, which includes use of a cushioned wedged insole. The medial wedged insole can selectively reduce forces from a lateral joint compartment, such as the lateral knee compartment; and a lateral wedged insole can selectively reduce forces from a medial joint compartment, such as the medial knee compartment. As such, medial wedges may treat or prevent arthritis in lateral compartments and lateral wedges may treat or prevent arthritis in medial compartments of joints. Further, a combined treatment may include alternating use of a medial wedge and a lateral wedge. Combined treatment may selectively redirect forces away from lateral or medial compartments to provide a more comprehensive treatment.

In another aspect of the present invention a method of treating osteoarthritis is provided through the use of the cushioned wedged insole. Use of the cushioned wedged insole may increase proliferation of cartilage aggregates or may increase cartilage production. In further embodiments, the method also includes administration of a pharmaceutical such as injection of a corticosteroid medication into the arthritic joint. In some embodiments, hyaluronic acid or a hyaluronic acid derivative is injected into the arthritic joint. In some embodiments HYALGEN (sodium hyaluronate) or SYNVISC (hylan G-F 20) is injected into the joint. In some embodiments, the cushioned wedged insole is provided in combination with an unloader brace.

In another aspect of the present invention the cushioned wedged insole is used as a treatment for an ankle sprain. Exemplary sprains that may be treated are inversion and eversion injuries to the ankle. For example, in instances where an inversion force may tear the lateral ligaments the use of the cushioned lateral wedged insole would be used to restrict the inversion while keeping the tension off the previously damaged lateral ligaments.

In another aspect of the present invention a method of reducing forces applied to a weight-bearing joint of a subject during a golf swing is provided through the use of a cushioned wedged insole, chambered insole or golf shoe including the insole is provided. The method includes use of an insole provided herein that cushions and reduces axial or redirects mediolateral forces at impact of a golf ball. In some embodiments, the cushioned insole is a medial wedged insole. In still other embodiments, the lateral wedged insole is provided. In still other embodiments, a chambered insole is provided.

In another aspect of the present invention cushioned wedged slabs or cushioned wedged insoles are used to unload and protect a recent surgical compartment after performing an operation or for rehabilitation.

BRIEF DESCRIPTION OF THE DRAWINGS

Those of skill in the art will understand that the drawings, described below, are for illustrative purposes only. The drawings are not intended to limit the scope of the present teachings in any way.

FIGS. 9A-C provides a series of bar graphs depicting changes in peak force on both medial and lateral compartments of the knee using various devices during the takeaway, impact and follow-through phases of the golf swing. “Normal Shoe Neutral” indicates no wedge; “3° Brace” refers to a 3 degree unloader brace; “2.5 M Wedge” refers to a 2.5 degree medial wedge; “5.0 M Wedge” refers to a 5 degree medial wedge; “Spiked Shoe Neutral” refers to spiked golf shoes alone with a neutral balance insole; “On Rough” indicates that the data was collected on golf swings where the golfer hit through the “rough” (areas of increased grass length) as opposed to the fairway.

In FIGS. 15A-B the control is bare foot. "Canadian" is an insole used by Canadian Military, Sorbothane is a polyurethane gel like proprietary insole. "StingFree" is commercial insole that allegedly absorbs shock. "2.5 LW" is EVA with 2.5 degree slope lateral wedge. "2.5 MW" is EVA with 2.5 degree slope medial wedge. "5 LW" is EVA with 5 degree lateral wedge. "5 MW" is EVA with 5 degree medial wedge.

DETAILED DESCRIPTION OF THE INVENTION

Detailed descriptions of the preferred embodiments of the present invention are provided herein. It is to be understood; however, that the present invention can be embodied in various forms. Therefore, specific details disclosed herein are not to be interpreted as limiting, but rather as the basis for the claims and as representative basis for teaching one skilled in the art to employ the present invention in virtually any appropriate detailed system, structure, or manner.

A. DEFINITIONS

The term "lateral wedge" or "lateral wedged insole" refers to a cushioned wedged slab 12 or cushioned wedged insole 22 characterized as having an upper edge 14 or thicker edge that generally follows the outer length or contour of the foot. The lateral wedged insole is not required to follow the exact contour of the foot and need not extend the entire length of the foot. Preferably the lateral wedged insole extends at least one half the length of the foot and more preferably from the subject's heel to the metatarsal heads.

The term "medial wedge" or "medial wedged insole" refers to a cushioned wedged slab 12 or cushioned wedged insole 22 characterized as having an upper edge 14 or thicker edge that generally follows the inner length or instep of the foot. The medial wedged insole is not required to follow the exact contour of the foot and need not extend the entire length of the foot. Preferably the medial wedge extends at least one half the length of the foot and more preferably from the subject's heel to the metatarsal heads.

The term "heel wedge" refers to a conventional wedge shape used under the heel that does not extend substantially beyond the heel. A heel wedge does not extend to about the middle of the foot.

The term "wedged configuration" or "wedge configuration" refers to a general wedge shape, which includes an upper edge, a lower edge and a slope. The slope of a wedge may be linear or may be arced such as generally convex or concave.

The term "joint compartment" refers to a subset of a joint, which for instance is either towards the median plane of the body or a "medial compartment" or towards the lateral portion of the body or a "lateral compartment." The knee and ankle both include a "medial compartment" and a "lateral compartment."

The term "mediolateral forces" refers to the distribution of forces between a medial compartment of a joint and a lateral compartment of a joint.

Figure 12:
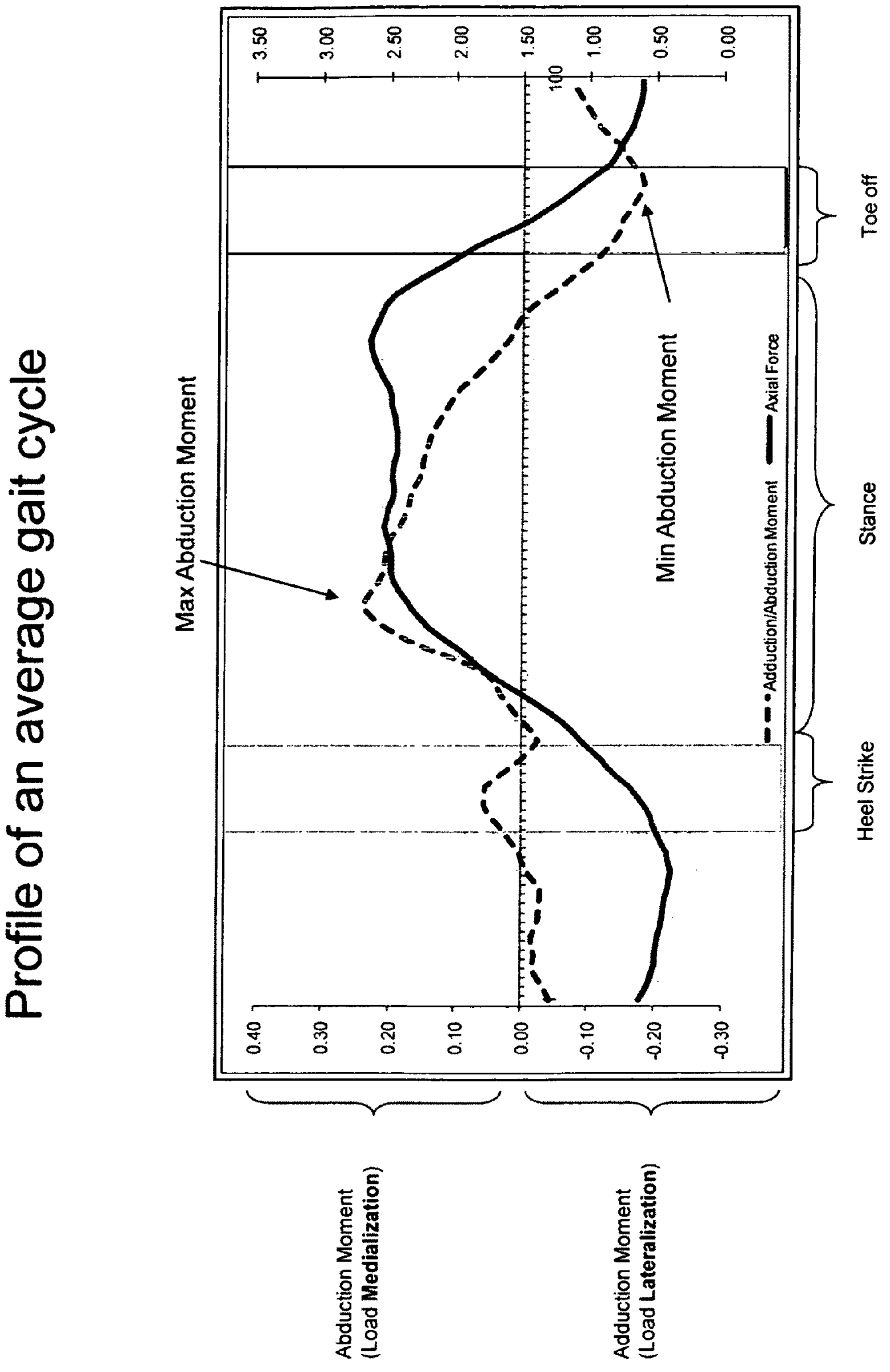
FIG. 12 is a bar graph depicting the profile of an average gait cycle including abduction moments during heel strike, stance and toe off.

The term "axial forces" refers to forces exerted generally parallel to an axis. Axial forces include downward or upward forces exerted on the weight-bearing joints, such as at heel strike and take off during gait. Exemplary forces for heel strike, stance and toe off are provided in FIG. 12.

The term "partial collapse" refers to the compression of an insole that retains its general shape. In the case of wedged insoles 22, a partial collapse refers to the compression of the insole 22 while retaining a general wedged configuration. Preferably, the slope remains about the same, or within about 20%; however the thickness of each end of the wedge typically changing during compression.

B. INTRODUCTION TO THE INVENTION

As previously introduced, conventional heel wedges are not widely accepted as effective treatments for reducing load on weight-bearing joints. This is likely due in part to unreliable testing techniques employed in traditional studies. For example, most studies rely on video or force plates to determine whether experimental devices are helpful in reducing axial forces such as jarring during running or normal gait. As such, the results are circumstantial, open to interpretation and thus imprecise. A recent technology, referred to as an electronic knee or "E-knee" has been developed that not only accurately measures peak axial loads on weight-bearing joints in vivo but also more precisely studies the in vivo forces between sub-compartments of a weight-bearing joint. Morris et al., Journ. of Bone and Joint Surg. (American) 83:S62-66 (2001). The F-knee is available to some subjects that undergo total knee replacement surgery and can precisely measures forces within each of the medial and lateral compartments of the knee. This recent testing method provides real time in vivo testing data of peak axial forces and mediolateral forces (distribution of peak force across the medial and lateral compartments of the knee). Using this method, studies provided herein demonstrate that not only peak axial forces can vary during activities but also peak forces within medial compartments and lateral compartments of weight-bearing joints can also widely differ. Among the findings provided herein it is surprisingly revealed that even activities previously considered low impact, such as golf, can generate significant forces on the body, which can result in injury. As such, these methods are able to accurately test a variety of materials and configurations designed to reduce loads on weight-bearing joints or compartments therein and thus provide accurate testing for improved preventative and therapeutic devices or treatments. E-knees for both left and right knees were used during testing. Further, subjects having the E-knee were used to test a variety of devices for the cushioning and redistribution of peak forces during the golf swing in and out of the rough. Surprisingly, devices are now disclosed herein that can selectively reduce peak forces from medial and lateral compartments of weight-bearing joints.

Figure 1:
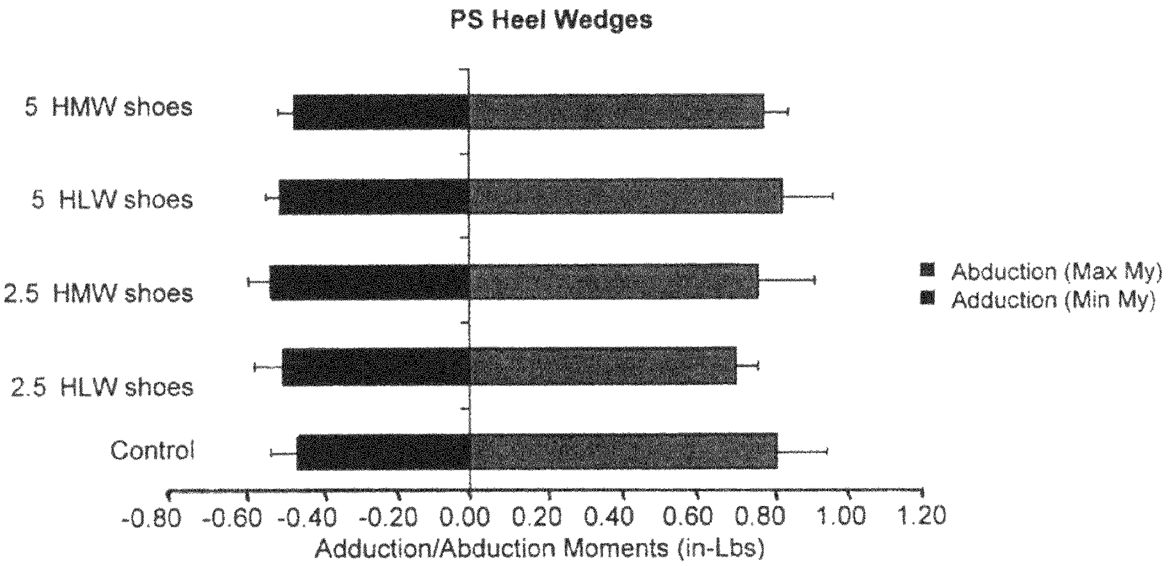
FIG. 1 is bar graph depicting the medial load and lateral compartment load using various heel wedges known in the art. “Control” is barefoot. 2.5 HLW is a 2.5 degree lateral heel wedge. 2.5 HMLW is a 2.5 degree medial heel wedge. 5 HLW is a 5 degree lateral heel wedge. 5 HMW is a 5 degree medial heel wedge.

An independent testing of whether or not heel wedges would effectively reduce axial load or shift mediolateral forces was initially conducted. Accordingly, a study was performed to assess the effectiveness of both medial and lateral heel wedges using the E-knee. The study included the use of 5 degree and 2.5 degree medial and lateral heel wedges. Specifically, heel wedges were tested in vivo with direct measurements for their ability to shift peak forces between the medial compartment and lateral compartment using the E-knee. The results, which are depicted in the bar graph shown in FIG. 1, verify the findings of the American Academy of Orthopedic Surgeons. That is, heel wedges do not appear effective at shifting peak forces across the medial or lateral compartments of the knee. However, wedges extending beyond the heel were also designed for testing. It was surprisingly found that while heel wedges themselves were not effective at shifting loads between mediolateral forces, longer lateral and medial wedges could be developed that selectively reduce or shift peak load between the medial compartment and lateral compartment of weight-bearing joints. Further, by providing an elongated insole, such as to about the metatarsal heads, cushioning is effective from heel strike, through stance and to step off forces on the metatarsal heads. The present invention documents this finding and provides effective and corresponding devices. Further, by studying the transfer of forces in barefoot subjects herein additional insoles have been developed that mimic the anatomical structure of the pad on the sole of the foot and provide improved reduction of axial forces.

C. WEDGED SLABS AND WEDGED INSOLES

Embodiments of the present invention provide cushioned wedged slabs 12 and cushioned wedged insoles 22 that reduce peak load such as impact from one's body weight on weight-hearing joints, such as the knees, ankles, hips and spine. The cushioned wedged slabs 12 and insoles 22 reduce impact forces using a combined approach. First, the cushioned wedged slab 12 or insole 22 provides a cushion which softens the impact on the joint. Second, the wedged insole 22 redirects forces away from the affected joint or affected compartment of the joint, which dissipates or shifts the forces. Accordingly, when the body is exposed to increased forces such as during sporting activities, cushioned wedged slabs 12 and insoles 22 can reduce the likelihood of injury by dissipating the force away from the primary affected area. Further, by redirecting forces across the entire joint the cushioned wedged slabs 12 and insoles 22 increase balance and increase muscle building efficiency. When the body suffers from joint-associated medical conditions, such as osteoarthritis, the cushioned wedged slabs 12 and insoles 22 reduce peak forces on the arthritic joint or arthritic compartment and thus encourage regrowth of cartilage.

Figure 2A:
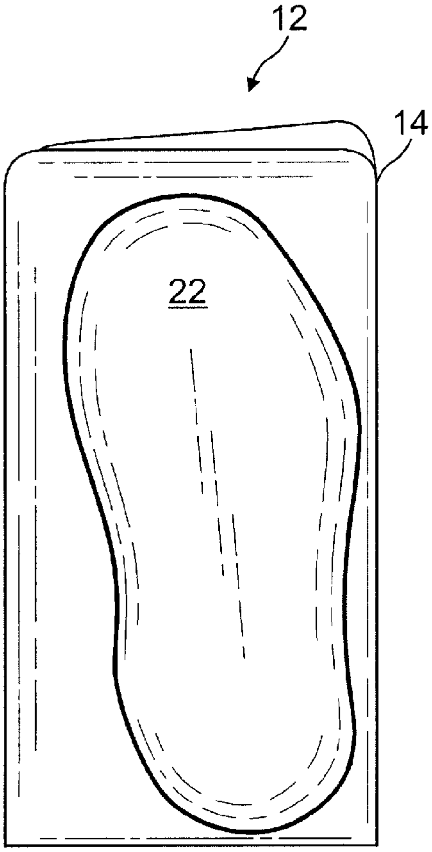
FIG. 2A depicts a cushioned wedged slab 12, from which a cushioned wedged insole 22 is formed. The upper edge 14 or thicker edge of the cushioned wedged slab 12 is positioned along the outer length of the cushioned wedged insole 22 to form a lateral wedge.
Figure 2B:
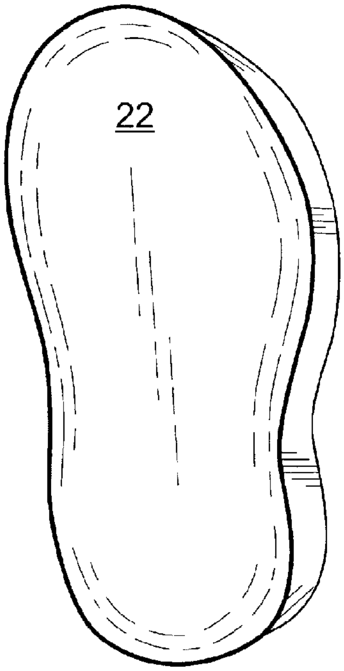
FIG. 2B depicts the cushioned wedged insole 22 removed from the cushioned wedged slab 12 shown in FIG. 2A to form a lateral wedge for the right foot.
Figure 3:
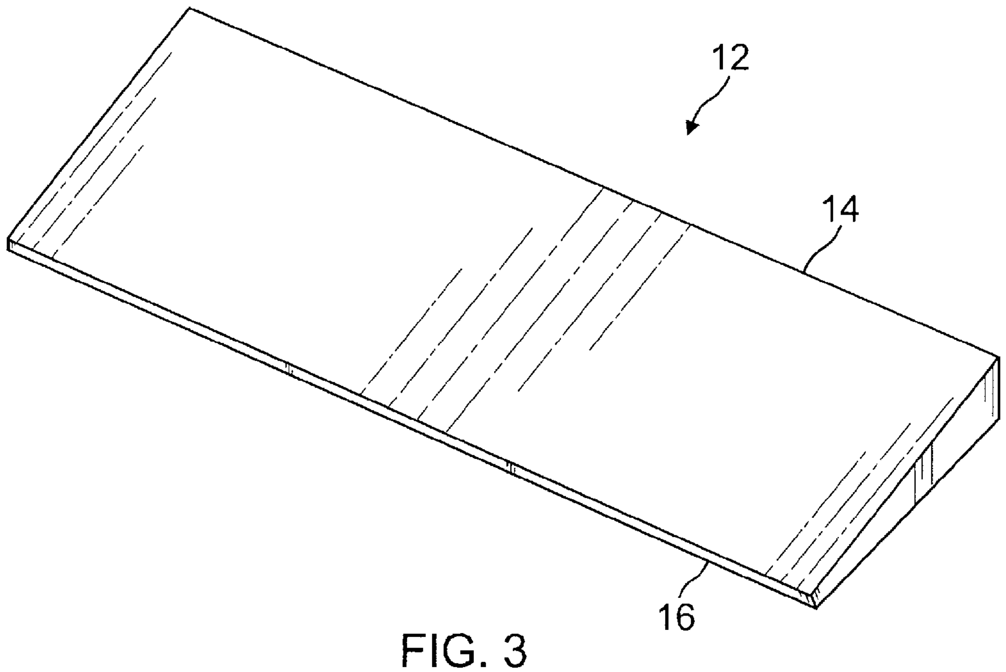
FIG. 3 is a perspective view of a cushioned wedged slab 12 clearly depicting the upper edge 14 and lower edge 16.
Figure 4:
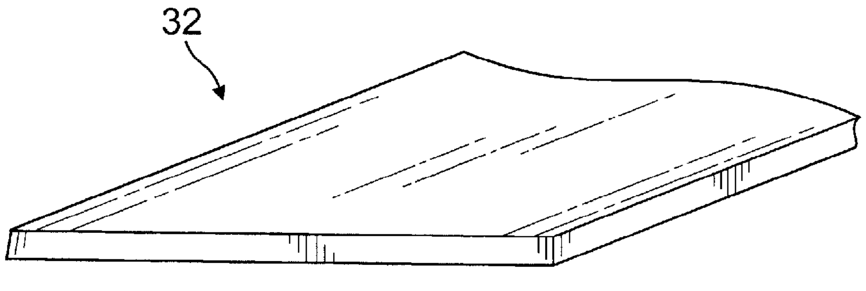
FIG. 4 is a perspective view of a neutral balance slab 32.
Figure 5:
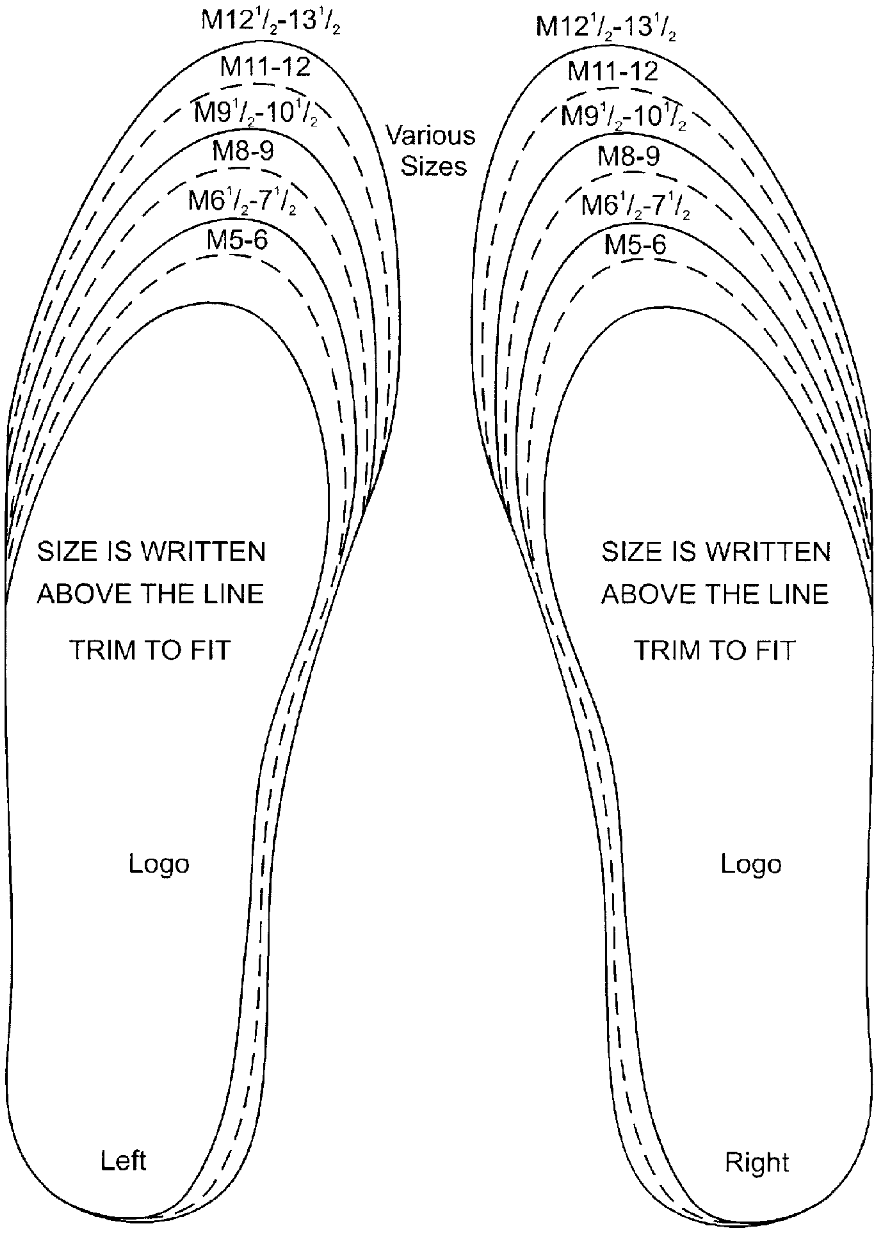
FIG. 5 depicts a sizing diagram for use with the cushioned wedged slab 12 or cushioned wedge insole 22 for cutting the desired shoe size.

In preferred embodiments the cushioned wedged slab 12 is configured for placement underneath the foot, such as within a subject's shoe, slipper, boot or the like. Most preferably, the wedged slab 12 is configured as an insole or a wedged insole 22 extending from about the heel to the metatarsal heads. In some embodiments the length varies from about three inches to about twelve inches. Preferably the measurements are about 4.25 inches wide by about 14 inches in length, which may be further enlarged or shortened to accommodate most any foot. Thus, sizing may vary according to the length of the subject's foot. The wedged insole 22 both cushions or absorbs impact forces and deflects or redirects the forces away from the affected joint or joint chamber and thus reduces the chance of injury and encourages the production of cartilage. Constructing or shaping the cushioned wedged insole 22 from the cushioned wedged slab 12 allows for customization of desired slope and wedge thickness. For example, referring to FIGS. 2A and 2B, the viscoelastic material of the cushioned wedged slab 12 can be cut, such as with scissors, to be configured to accommodate the person's anatomy and or pathology and to fit inside a user's footwear. Although a variety of methods can be used to produce the desired size, in some embodiments, a sizing chart, such as depicted in FIG. 5 may be provided in a suitable kit, which may also include the neutral balanced slab 32 as depicted in FIG. 4, which may be used in the other shoe. One skilled in the art will now recognize the wedged slab 12 may be personally shaped to the user's unique foot anatomy, any pathology and to the geometry of any specific shoe. Thus, the wedged slab 12 can be provided as a single wedge from which the user can form right, left, medial or lateral wedges thereby reducing inventory and/or product lines of multiple sizes. In addition, the wedged slab 12 can be combined with a neutral balance slab 32 to produce an insole having any desired configuration.

The cushioned wedge insole 22 may be configured for placement in any shoe, boot, slipper and the like as needed. In some embodiments, the cushioned wedged insole 22 is used in athletic shoes including golf shoes, running shoes, tennis shoes, cleated shoes, such as baseball, football and soccer cleats and the like whenever increased load is present or expected. The cushioned wedged insole 22 and shoes incorporating the cushioned wedged insole 22 prevent and treat injury to knee, ankle, foot and hip.

Depending on the needs of the user, the cushioned wedged insole 22 may be shaped to provide a lateral wedge or a medial wedge. The lateral wedge aligns the upper edge along the general path of the outer length of the foot. In contrast, the medial wedge aligns the upper edge of the wedge generally along the inner length of the foot or along the foot insole. By selecting either the lateral wedge or medial wedge, peak forces are selectively reduced from inner compartment or outer compartment of the joint. Thus, the lateral wedge or lateral wedged insole is preferred when reducing forces from medial compartments, such as the inner knee or inner ankle, and the medial wedge or medial wedged insole is preferred when reducing forces from lateral compartments, such as the outer knee or outer ankle.

In preferred embodiments the cushioned wedged insole 22 is constructed from viscoelastic material, which is able to compress under pressure and rebound when pressure is reduced. In the preferred embodiments, the cushioned wedged insole 22 or slab 12 is constructed from a closed cell foam and more preferably EVA foam. Other preferred materials would have characteristics similar to EVA foam. EVA foam is found to have a plurality of encapsulated chambers of gas or air that can be used to mimic the fatty globules found in the foot. Further, like fibrous tissue that surrounds and provides support to the fatty globules, EVA foam prevents the collapse of the encapsulated pockets and thus combines cushioning with support. As such, preferably the cushioned wedged insole is constructed from materials that can mimic the cushioning and support found anatomically within the foot, namely the combination of fatty globules with surrounding and restricting fibrous tissue. As such, modifications to foams such as EVA foam that provide the disclosed properties are also encompassed by the present invention. Although both the outer edge and inner edge of the cushioned wedged insole 22 may compress, the insole 22 retains its wedged configuration even during compression. That is the cushioned wedged insole 22 partially compresses to absorb, dissipate and redirect forces yet does not completely collapse into a flat configuration under normal use and thus retains a slope greater than about 0.5 degrees. Accordingly, even when compressed the cushioned wedged insole 22 continues to redirect forces away from the affected joint or joint chamber.

Viscoelastic materials exhibit both viscous and elastic characteristics when undergoing compression. Viscous materials resist strain linearly with time when a stress is applied. Elastic materials strain instantaneously when compressed, and quickly return to their original state as the stress is removed. Viscoelastic materials possess elements of both of these properties and exhibit time dependent strain. These materials may be obtained from suppliers known in the foam and plastic arts.

The viscoelastic material can be made at least in part from of any suitable cushioning material with the described properties and characteristics. That is, while the material provides a cushioning it also must retain a wedged shape, even when compressed. Preferably, the material has sufficient durometer (hardness) and possesses a physical memory, meaning that it returns to its original shape after the forces of compression are removed, readying it to accept the impact of the patient's next step and provide cushioning. Thus, while time for return to its original shape can vary, the shape should return prior the user's next step. In certain embodiments, the material returns to its original shape immediately, or substantially immediately, or within a time period, such as, for example, less than about 1 second. In some embodiments, the material returns to its original shape within about 500 milliseconds to 1 second. In other embodiments, the material returns to its original shape within about 100 milliseconds to 500 milliseconds. In some embodiments, the material returns to its original shape in a mass-dependent manner, such that thicker areas of the wedged insole 22 return to their original shape more slowly than thinner areas. In certain embodiments, any material possessing the desired mechanical properties of the insole 22 (apparent density, Asker hardness, resilience, stiffness, compression set, compression fatigue, water vapor permeability and perspiration resistance) can be used in its construction.

In preferred embodiments, the cushioned wedged insole 22 is of homogeneous construction. Most preferably, the cushioned wedged insole 22 is constructed from a closed cell foam having the desired characteristics and most preferably is formed from Ethylene vinyl acetate (CAS# 24937-78-8, also known as EVA), which is the copolymer of ethylene and vinyl acetate, or a modification of the EVA having the desired properties. The weight percent vinyl acetate usually varies from about 10 to 40%, with the remainder being ethylene. EVA is a polymer found to provide desirable elastomeric properties and provides desired softness and flexibility.

Figure 15A:
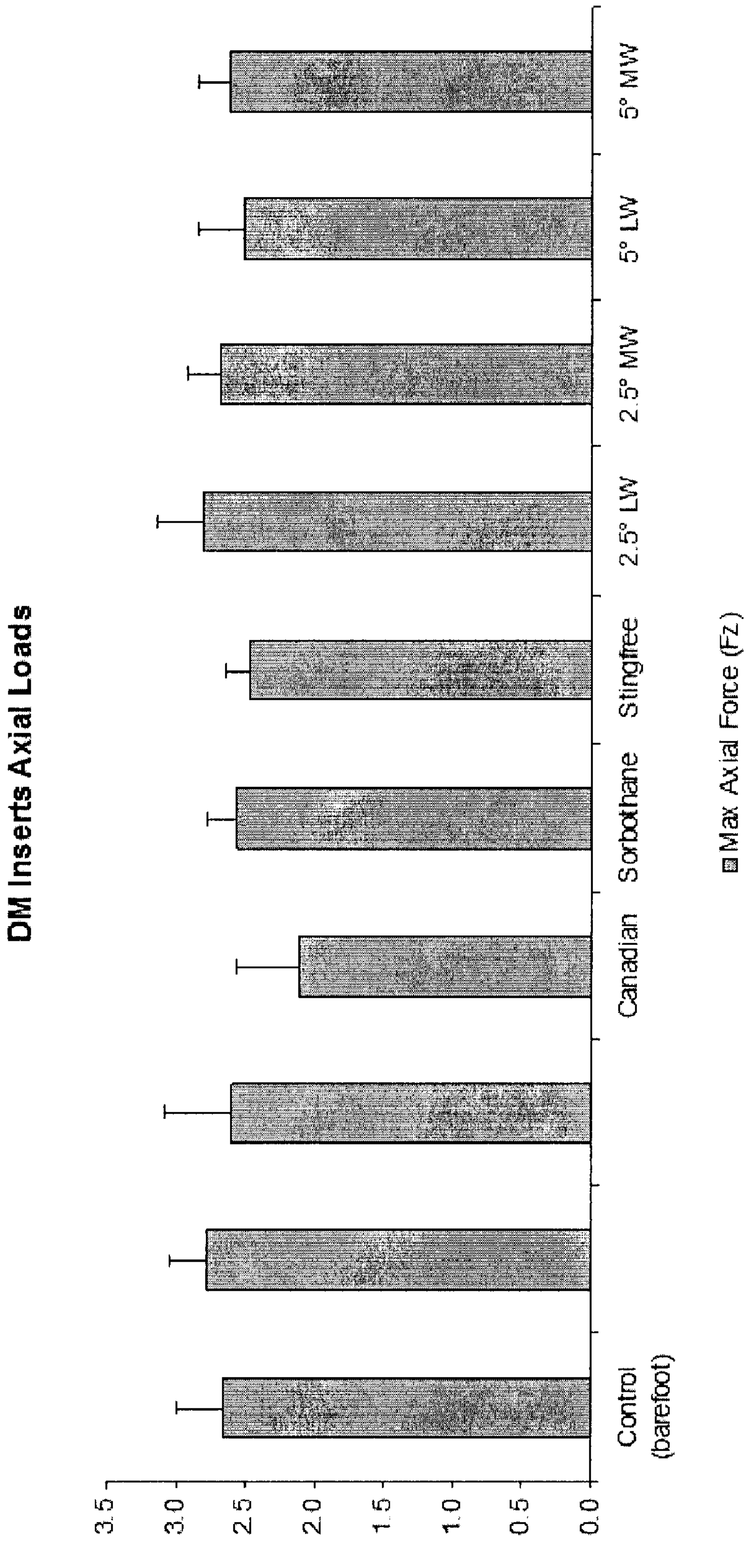
FIG. 15A is a bar graph depicting peak axial loads on the knee measured in vivo by a total knee implant with load sensors.

Materials such as gels, including Sorbothane and PORON, a microcell urethane, were also tested for their ability to absorb impact without bottoming out or flattening out and thus considered for their applicability for homogenous construction of a cushioned wedged insole 22. Studies found that gels like Sorbothane and the microcell urethane PORON routinely bottomed out and were thus too soft to use alone. That is, neither Sorbothane nor PORON would retain a wedged configuration when compressed and thus would not likely be desirable for cushioned wedged insoles 22. One such series of studies are summarized in FIG. 15A, which summarizes total or peak axial load and FIG. 15B, which further studies peak medial compartment load compared to peak lateral compartment load. As depicted in FIG. 15A, Sorbothane does not reduce peak axial loads, when compared to bare feet. It is believed Sorbothane does not reduce peak axial loads because it compresses too quickly resulting in bottoming out. Similar results were observed when studying open cell foam, such as PORON, which is offered in conventional or athletic shoes. FIG. 15A also shows 5 degree EVA provides slightly better reduction of peak axial load compared to barefeet. Although gel materials such as Sorbothane and open cell foams would not be desired in a homogenous construction of a cushioned wedged insole 22, they can potentially be combined with additional materials in a heterogeneous construction substantially as set forth below. PORON was also found to be relatively expensive compared to EVA and thus would be less desirable for other reasons to the ordinary consumer. It is also believed that EVA is more economical to be formed into a cushioned wedged slab 12. As such, EVA is most preferred material for homogenous construction. EVA material or a modified elastomer thereof preferably facilitates slab and wedge manufacture.

In some embodiments, the cushioned wedged insole 22 is of heterogeneous construction. In heterogeneous embodiments, the cushioned wedged insole 22 can comprise two materials, three materials, or more. For instance, the cushioned wedged insole 22 may include an inner rigid wedged material to redirect forces and a cushioned outer covering to absorb impact and to soften the interface between the subject and the rigid wedged material. In some embodiments rigid materials mimic the encompassing fibrous anatomical features of the foot and soft materials mimic fatty globule anatomical features of the foot. Materials may be combined in any desired configuration, such as by adhesive, hook and loop (such as VELCRO) and the like. Further, the cushioned wedged insole 22 may include a cover, such as a cover having antimicrobial or antifungal properties to prevent growth of microbes, fungus and the like. In addition, a cover or cushioned wedged insole 22 may include a surface to enhance traction. Covers may be integral, or attached to the wedged insole 22 or may be removable, such as for washing separately.

In some embodiments heterogeneous construction yields an insole with properties that closely mimic the natural foot. The sole of the natural foot has multiple chambers of fat surrounded by a network of fibrous tissue. The compression of the chamber is restricted from bottoming out by the surrounding fibrous tissue, thus providing a damping and dissipating effect upon the load applied. For instance, by combining members constructed from materials such as plastics together in a chamber with soft materials, the fibrous and fatty layers of the foot can be closely duplicated. Alternatively, the fibrous and fatty layers of the foot can be duplicated or mimicked by providing rigid chambers in desired alignment with soft chambers. Further, by selectively arranging these chambers, optionally having different ratios of rigid to soft material, complex anatomical structures can be generated to reduce or dissipate peak axial forces or redirect mediolateral forces. Rigid materials are considered to be those that do not substantially deform under conventional loads; whereas soft materials generally do compress under conventional loads. Fluid materials may be rigid or soft depending on the pressurization within a capsule or the elasticity of a capsule itself.

Since the cushioned wedged insole 22 may be formed from the combination of two or more materials, in some embodiments, the cushioned wedged insole 22 may be constructed in part from a variety of plastics, foams or the like. In embodiments that include plastic materials, the plastic materials can include, for example, thermoplastics, such as, for example, acrylonitrile butadiene styrene plastics (ABS), acetals, acrylic (Perspex), acrylo-nitrile (nylon), cellulosics, fluoroplastics, high-density polyethylene (HDPE), low-density polyethylene (LDPE), Noryl, polyarylates, polyarylsulfones, polybutylenes, polybutylene terepthalate (PBT), polycarbonates, polyesters, polyetherimides, polyetherketones, polyethylene (polythene), polypropylene, polyallomers, polyethylene terephalate, polyimides, polyamide-imides, poly vinyl acetate (PVA), poly vinyl chloride (PVC), polystyrene, polysulfones, Styrene, ABS PTFE (Teflon), ENGAGE and the like. Typically, the plastics may be used as a more rigid layer over which a softer cushion layer may be applied.

In embodiments that include plastic materials, the plastic materials can be, for example, thermosets, such as, for example, alkyd polyesters, allyls, bakelite, epoxy, melamine, phenolics, polybutadienes, polyester, polyurethane, silicones, ureas, and the like. Likewise, the plastic materials can include bioplastics. Bioplastics are a form of plastics derived from renewable biomass sources, such as vegetable oil, corn starch, pea starch, or microbiota, rather than traditional plastics that are often derived from petroleum. Types of bioplastics suitable for use with embodiments of the invention include, for example, polylactide acid (PLA) plastics, poly-3-hydroxybutyrate (PHB), polyamide 11 (PA 11), bio-derived polyethylene, and the like. Such materials are known in the plastic arts and can be molded according to known methods such as injection molding and the like.

In embodiments that include foam materials, the foam can be, for example, polyurethane foam (foam rubber), polystyrene foam, or the like. In embodiments utilizing polyurethane foam, the type of polyurethane foam can be, for example, elastomers, including, EPM (ethylene propylene rubber, a copolymer of ethylene and propylene) and EPDM rubber (ethylene propylene diene rubber, a terpolymer of ethylene, propylene and a diene-component), Epichlorohydrin rubber (ECO), Polyacrylic rubber (ACM, ABR), Silicone rubber (SI, Q, VMQ), Fluorosilicone Rubber (FVMQ), Fluoroelastomers (FKM, and FEPM) Viton, Tecnoflon, Fluorel, Aflas and Dai-El, Perfluoroelastomers (FFKM) Tecnoflon PFR, Kalrez, Chemraz, Perlast, Polyether Block Amides (PEBA), and Chlorosulfonated Polyethylene (CSM). Depending on the characteristics of the foam, it may be acceptable to combine a soft foam or open cell foam over hard or rigid foam to produce a cushioned wedge. In embodiments utilizing polystyrene foam, the type of polystyrene foam can be, for example, expanded polystyrene foam, and extruded polystyrene foam, or the like. In embodiments of extruded polystyrene foam (XPS), the XPS foam can be, for example, Styrofoam, or the like.

The cushioned wedged insole 22 is provided in a wedged configuration, which provides an upper edge having greater thickness than a lower edge. Determining the appropriate thickness of the wedged slab 12 or insole 22 may be performed by a physician treating the subject or a technician. The thickness determination may involve considerations of the patient's age, weight, condition of the knee, ankle, hip and the like. Further, evaluation of proposed sporting activities or estimated loads therefrom may be considered. Though non-limiting, cushioned wedged insoles 22 having greater thickness may be desired when participating in sporting activities resulting in higher loads on the body. Thus, activities such as running may indicate a thicker cushioned wedged insole 22 would be preferable as opposed to activities such as short distance walking; however, this is for guidance and not requirement.

As an example, a variety of insoles were tested for their use in golf. The examples demonstrate medial wedged insoles having a 2.5 degree slope or 5.0 degree slope reduced peak forces within the lateral compartment of the knee during impact of the golf ball and followthrough. Results may be seen in FIGS. 8-10. Medial wedges having 5.0 degree slope provided the greatest reduction in peak force on the lateral compartment. Thus, as guidance medial wedges having a slope from about 2.5 degrees to about 5.0 degrees may be preferred and wedges having a slope of about 5.0 degrees may be most preferred. However, while these provide guidance or a basis for consideration, individual optimization of medial or lateral wedges may be preferred on a subject by subject basis.

Figure 11A:
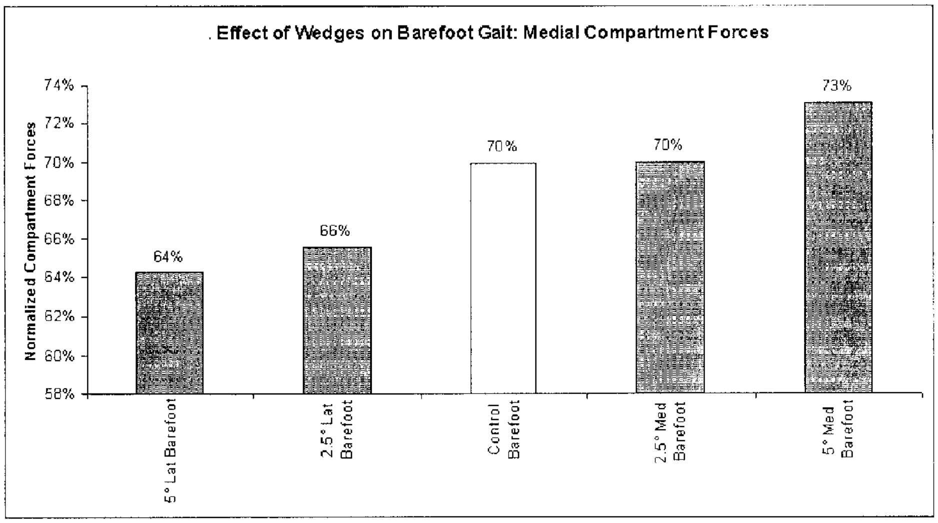
FIG. 11A is a bar graph depicting the effect of cushioned wedge insoles on maximum medial compartment forces on normal barefoot gait. The test subject wore stockings only, while placing inside the stocking the lateral or medial wedge insoles of 2.5° or 5°.
Figure 11B:
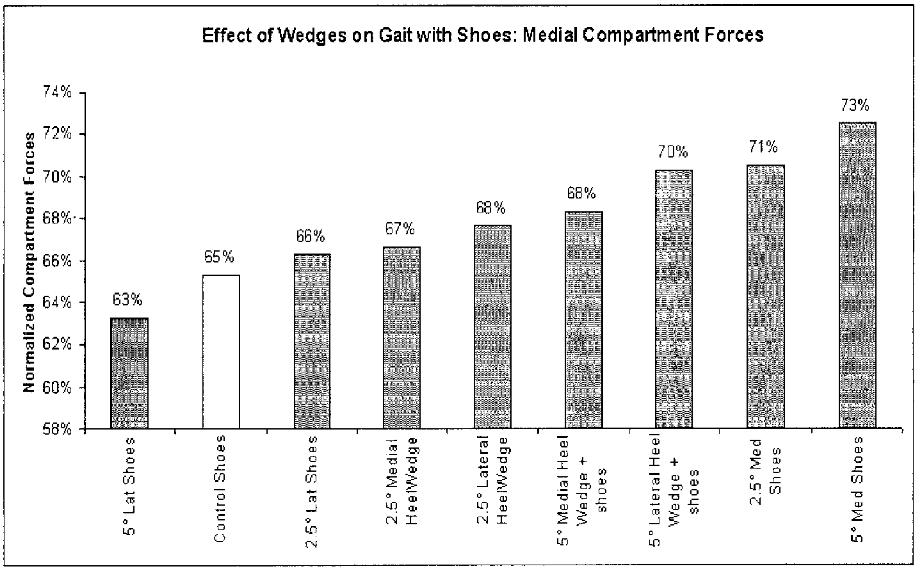
FIG. 11B is a bar graph depicting the effect of cushioned wedged insoles on maximum medial compartment forces on normal gait when wearing shoes. The test subject wore shoes, while using lateral or medial wedged insoles or heel wedges of 2.5° or 5°.

Cushioned insoles were also tested for their applicability to reduce load during normal gait. Referring to FIGS. 11A-B, the 5.0 degree lateral wedges appeared to reduce the majority of peak load from the medial compartment during regular gait in tested subjects. Peak forces exerted during normal gait are shown in more detail in FIG. 12, which demonstrates abduction forces during heel strike, stance and toe off. Forces are shown to significantly increase between heel strike and stance and decrease at about toe off.

Extensive testing of 5 degree wedged insoles was performed using a cushioned wedged insole having a thicker end of about 14 mm and a thinner end of about 4 mm. Testing of the 2.5 degree wedged insole was performed using a cushioned wedged insole having a thicker end of about 7 mm and a thinner end of about 4 mm. Although wedges having the referenced dimensions are preferred, the thickness of the cushioned wedged slab 12 or insole 22 may be adjusted to alter the slope of the cushioned wedged insole 22. Selectively altering the slope angle may further permit the redirection of forces. Slopes greater than about 10 degrees are not generally preferred since they tend to be less comfortable. However, slopes of about 10 degrees may effectively shift mediolateral or axial forces and thus would be encompassed by the present invention. Wedged insoles 22 having a slope greater than 10 degrees may be provided with increased cushioning to assist in comfort.

Although nonlimiting, in some embodiments the upper edge 14 or thicker edge of the cushioned wedged slab 12 or cushioned wedged insole 22 can measure, for example, between about 7 mm to about 14 mm. In other embodiments, the thickness of the upper edge 14 measures about 4 mm to about 7 mm. In other embodiments, the thickness of the upper edge 14 measures about 14 mm to about 20 mm. In other embodiments, the upper edge 14 is greater than 20 mm thick. The thickness of the wedged slab 12 may vary at least in part due to the material used. That is, while 7 mm to 14 mm wedges are demonstrated as preferred, these are particularly preferred when using EVA. Thus alternative materials may result in different preferred dimensions. The determination of such will be within the abilities of the ordinary skilled artisan in view of the present invention.

Although nonlimiting, in some embodiments the lower edge 16 or thinner edge of the cushioned wedged slab 12 or cushioned wedged insole 22 can measure, for example, about 4 mm. In other embodiments, the thickness of the lower edge 16 measures about 2 mm to about 4 mm. In other embodiments, the thickness of the lower edge 16 measures about 4 mm to about 10 mm. In the present invention when using EVA foam the preferred thickness of the lower edge 16 is about 4 mm; however, the present invention encompasses any suitable dimension that provides and retains a wedged configuration during regular use and provides cushioning.

In some embodiments, the slope or line delineating the angle between the thicker and thinner edges of the cushioned wedged insole 22 can be, for example, between about 2.5 to about 5.0 degrees, between about 1 degree and 2.5 degrees, between about 5 degrees and 10 degrees and the like. Again, when using EVA, the preferred slope is from about 2.5 degrees to about 5 degrees and most preferably about 5 degrees. Slopes over about 10 degrees are less favored since they may cause patient discomfort. While exemplary slopes are provided, the actual slop may be greater or lesser and may be altered when using materials other than EVA. Although exemplary slopes are provided, they are provided as guidance thus may be altered within the spirit of the invention. Further, the slope need not be consistent across the entire wedged insole 22. That is there may be concave or convex areas of the cushioned wedged insole 22. Further, chambers such as those including a heterogeneous mixture of rigid and soft or malleable materials may be included within or form part of the cushioned wedged insole 22 to further mimic or support the anatomical structure of the foot to assist in comfort or unloading.

Since the cushioned wedged insoles 22 may be cut and contoured from the cushioned wedged slab 12, the cushioned wedged slab 12 may include an upper edge 14 having greater thickness than the desired cushioned wedged insole and a lower edge 16 having a lesser thickness than the desired insole. Accordingly, a variety of cushioned wedged insoles 22 having various thicknesses may be constructed from a single wedged slab 12.

Figure 6:
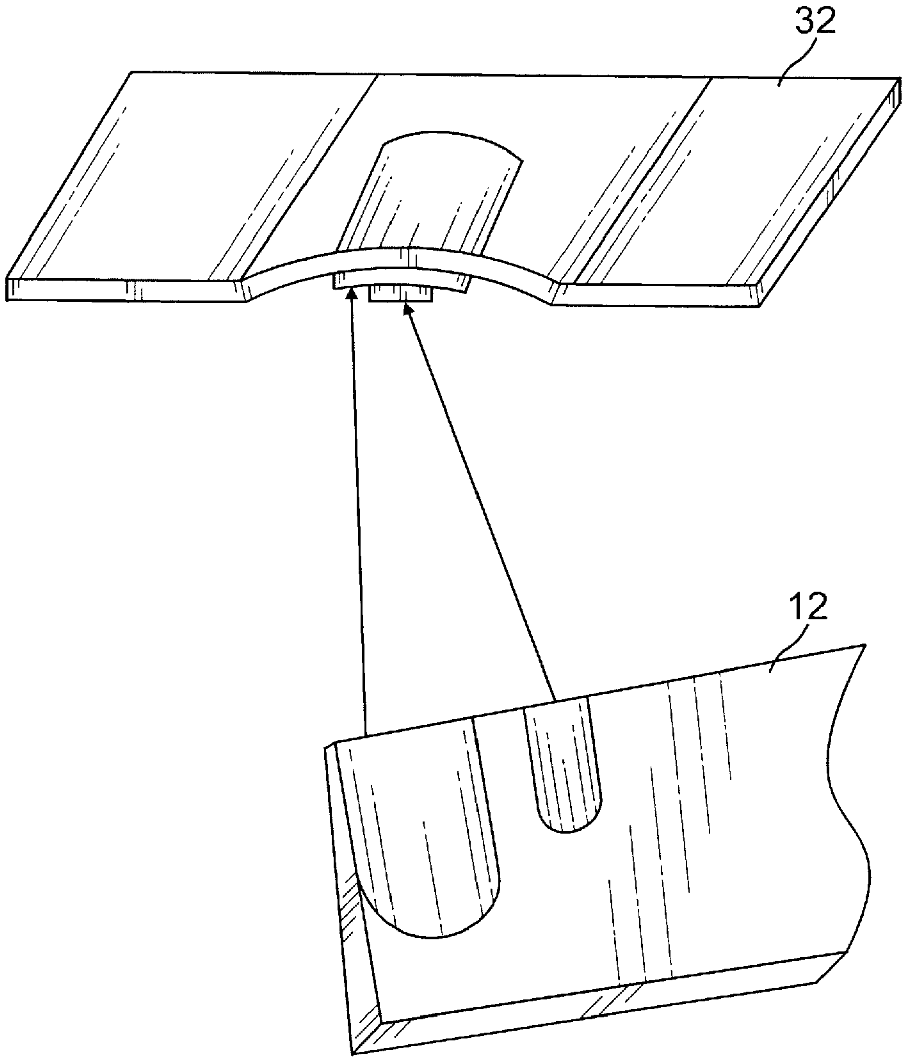
FIG. 6 shows a diagram depicting cutting from the cushioned wedged slab 12 to form additional arch support under a neutral balance slab 32.

In some embodiments the cushioned wedged slab 12 is provided as a component or part of a kit. Additional components may include a sizing chart for determining shoe size, such as depicted in FIG. 6, and a set of instructions. In preferred embodiments the cushioned wedged slab 12 is provided substantially rectangular allowing the removal of one or more wedged insole 22. As such, preferably the cushioned wedged slab 12 is greater than or equal to about 4.25 inches in width and about 14 inches in length. Typically variations in length will be more common than variations in width of the wedged slab 12 since generally the width of the wedged slab 12 defines in part the thickness of the wedged configuration; whereas the length may be extended to remove a plurality of insoles 22, whether medial or lateral. That is, since the wedged slab 12 has a wedged configuration, as the width increases so does the thickness or thinness of the wedged slab 12. The kit may also include a neutral balance insole 32. A neutral balance insole 32 is substantially flat, cushioned and not wedged. As such, the neutral balanced insole 32 may be formed to reduce forces from impact overall but is not particularly configured to shift mediolateral forces as in the case of medial wedges or lateral wedges. In some embodiments the neutral balanced insole 32 is constructed from MORON. The neutral balance insole 32 is typically placed in the second shoe to accommodate for the difference in height caused from the insertion of an insole 22 in the first shoe. As general guidance the neutral balance insole 32 typically has a thickness substantially the same as the lower edge or thinner edge of the wedged insole 22. In preferred embodiments, a neutral balance insole 32 having a thickness of about 3-4 mm was used.

Cushioned wedged slabs 12 may also be cut into a variety of configurations for use as heel wedges or as wedges against the metatarsals or ball of the foot. Further, as demonstrated in FIG. 6, slabs such as neutral slabs 32 or cushioned wedged slabs 12 may be combined to add arch support or provide any desired contour for the foot.

Cushioned wedged slabs 12 may also be adapted for use in other instances where the shilling or unloading of force is desired in combination with softening of force or cushioning. In some embodiments, the cushioned wedged slabs 12 are used in a helmet. Use in a helmet may provide additional cushioning while redirecting forces away from the site of impact such as to other cranial zones to prevent head or spine injury.

D. INSOLE HAVING A PLURALITY OF CHAMBERS MIMICKING FOOT ANATOMY

In another aspect of the present invention a chambered insole is provided, which contains a plurality of closed chambers that when combined replicate the anatomy of the foot. Specifically, a plurality of chambers, independently sealed, each containing media, preferably a heterogeneous mixture of a rigid and soft material, are combined replicate fibrous and fatty tissue in the body. Chambers, which are fluidly isolated from one another, may be arranged or layered to provide the desired configuration of fibrous to fatty layers. The chambers may be positioned in areas of the foot where fatty deposits should be found around the sole of the foot. Accordingly, the insole itself replicates a network of fatty cells restricted by the chamber barrier.

The chamber itself is constructed from an elastic material that can be selectively scaled. Exemplary materials are plastic polymers. The sealed chambers are then layered overtop one another to form a multilayer insole. Layering may be by directly positioning chambers over one another, placing chambers substantially adjacent to one another or a combination thereof. FIG. 18A provides an exemplary layer of isolated chambers provided in linear arrangement.

Chambers may be layered or selectively positioned to reduce axial forces such as peak loads or redirect mediolateral forces as provided herein. Thus by layering or positioning chambers complex anatomical structures having various densities and elasticities may be developed.

E. METHODS OF PREVENTING OR TREATING SPORTS INJURIES USING INSOLES THAT REDUCE LOAD ON WEIGHT-BEARING JOINTS

Sports injuries commonly affect professional athletes, amateur athletes as well as occasional weekend warriors. Sports injuries can be either acute (sprains, fractures, tears, etc.) or chronic (tendonitis, overuse, etc.). Almost everyone who exercises on a regular basis will suffer from a sports injury at some time or another.

The number and type of sports injuries are as varied as the individuals involved in sports, but some injuries are more likely than others. Some of the most common affect the knees. The cause of knee pain can vary but can result from damage to the anterior crucial ligament (ACL), posterior cruciate ligament (PCL), medial collateral ligament (MCL) lateral collateral ligament (LCL). In addition, knee pain can result from torn knee cartilage, chondormalacia, osteoarthritis, tendonitis and ruptured tendons, and iliotibial band syndrome.

Often, damage to the knee occurs when participating in high impact sports. High impact sports are those characterized by intense and/or frequent wear and trauma of weight-bearing joints. Although damage to the joints can occur due to increased physical impact, increased risk of sports injuries occurs when the participant has insufficient balance and underdeveloped muscles. Improper balance can lead to fatigue, which is known to increase the likelihood of injury. Further, by compensating or overcompensating for the body's imbalance the efficiency of proper muscle development is decreased.

Insoles provided herein including cushioned wedged insoles 22 and cushioned wedged slabs 12 used to treat or prevent sports injuries by reducing impact to weight-bearing joints through cushioning and selectively redirecting forces away from the affected joint or joint compartment. Similarly, cushioned wedged insoles 22 may be used during rehabilitation of various injuries or after a surgical procedure. For example, wedged insoles 22 are useful as a post operative treatment to cushion and redirect forces away from a post operative compartment.

Further, the use of cushioned wedged insoles 22 improves proper balance and when used during exercise facilitates efficient muscle building. Cushioned wedged insoles 22 redirect threes across mediolaterial chambers, which results in a more even muscle building.

Figure 7A:
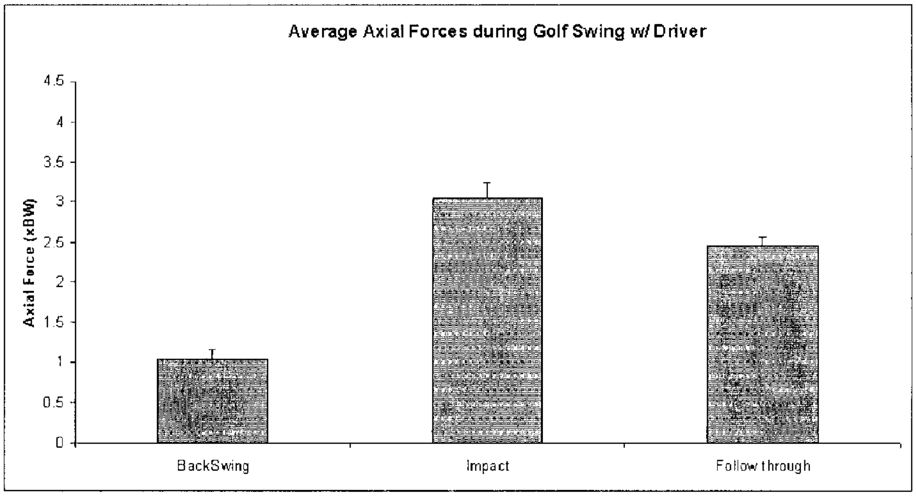
FIG. 7A is a bar graph depicting average axial forces generated during the golf swing using a driver compared to the subject’s body weight.
Figure 7B:
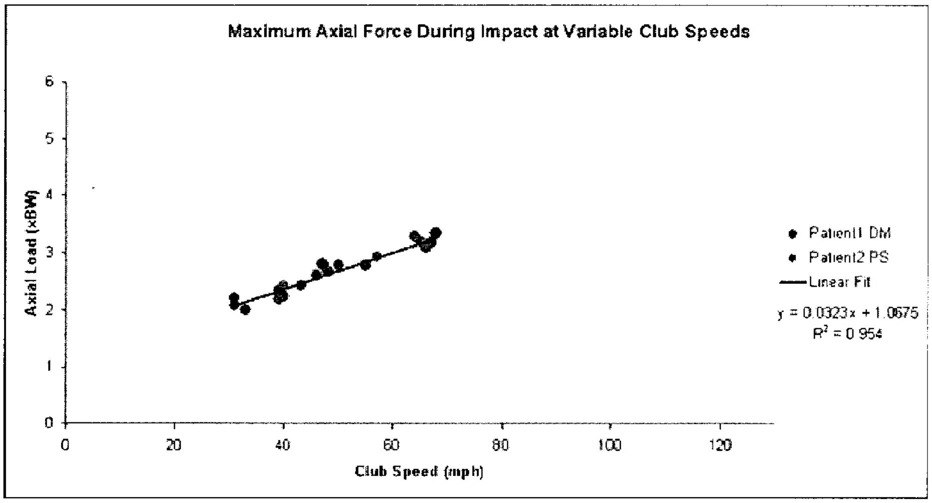
FIG. 7B is a plot demonstrating maximum axial force during impact at variable speeds of the golf swing.

Even those active in sports previously considered low impact are susceptible to injury. Golf is often considered a low impact sport; however even those active in golf are susceptible to injury of weight-bearing joints such as knees and hips. For example, the average golf swing increases loads on the body by about 3.5 to about 4.5 times the body's weight. As can be seen in FIG. 7A, an exemplary study demonstrated average axial force during the golf swing with driver for a tested subject was about 3 times the body's weight at impact and about 2.5 times the body's weight at follow through. Further, these loads are increased when increasing club head speed, when striking the ball from the rough, sand and the like. For example, FIG. 7B depicts a near linear relationship between axial load at impact and club speed, which was tested between about 30 mph and 70 mph using two subjects. Thus, while traditionally considered a low impact sport, golf can cause substantial wear on weight-bearing joints, especially for avid golfers. Thus regular wear on weight-bearing joints adds to the risk of injury to many regular golfers. Conventional unloader braces were tested for their ability to unload the weight-bearing joint; however, conventional unloader braces were not found effective statistically unless combined with the cushioned wedged insoles.

Medial wedged insoles are demonstrated herein to decrease peak loads on the lateral compartment of the knee about 15-20 percent during backswing, striking and follow-through. As described in the examples, both 2.5 degree medial wedges and 5.0 degree medial wedges were tested for their selective reduction of peak forces from the lateral and medial compartments of the knee joint across four patients having a total knee implant called an electronic knee or "E-knee." The E-knee is described by Morris et al., Journ of Bone and Joint Surg. (American) 83:S62-66 (2001). Results were converted to multiples of Body Weight (×BW) for comparison. Testing was also performed with a conventional unloader brace. As can be seen throughout the examples, the medial wedged insoles consistently and significantly decreased loads from the lateral compartment of the knee during the golf swing.

Figure 10:
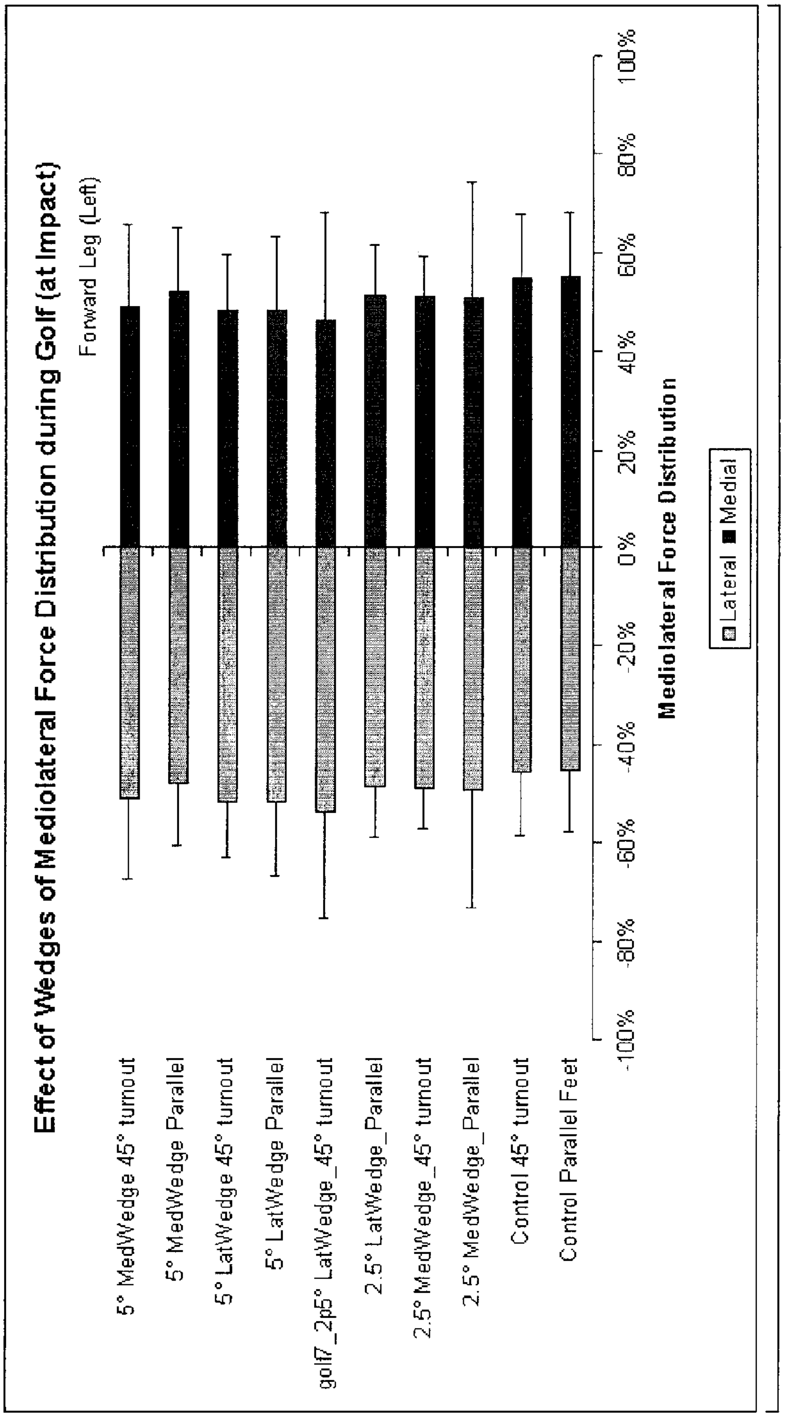
FIG. 10 is a bar graph depicting the effects of foot positioning (with or without wedged insoles) on peak mediolateral forces upon the knee at golf ball impact. Data is shown for the forward (left) leg of a right-handed golfer. “Turnout” refers to positioning the left foot to point approximately 45° towards the target rather than “Parallel,” in which the foot is positioned parallel to the right foot. “MedWedge” refers to use of a medial wedge. “LatWedge” refers to use of a lateral wedge. “5°” and “2.5°” refer to wedges having 5 degree and 2.5 degree slopes respectively.

Further, as shown FIG. 10, the use of lateral wedges and medial wedges were able to effectively redistribute the mediolateral forces incurred during the golf swing at impact, which is the most traumatic point of the golf swing. Specifically, lateral wedges were most effective at redistributing forces away from the medial compartment of the knee in the forward leg of the golfer.

Since cushioned wedged insoles 22 are shown to reduce loads during the golf swing, use of such insoles will reduce the likelihood of golf injury. Further, by incorporating the cushioned wedged insoles 22 or slabs 12 on the practice range, balance will be improved as well as the efficiency of muscle development increased.

Though exemplary sporting injuries are provided, the cushioned wedged insoles 22 may be used with many sports where weight-hearing joints are susceptible to increased loads. Thus, the cushioned wedged insoles 22 may be used to treat or prevent injury in high impact sports or low impact sports. By cushioning and selectively reducing load on the affected joint, the cushioned wedged insoles 22 and slabs 12 are able to reduce damaging forces and thus prevent injury and accelerate healing. As such, in nonlimiting embodiments, the cushioned wedged insoles 22 may be used for standing, dancing, walking, jogging, running, hiking, cycling, climbing, skiing, snowboarding, skateboarding, boxing, fencing, fishing, golf, tennis, baseball, basketball, soccer, rollerblading, skating and the like.

F. PREVENTION AND TREATMENT OF OSTEOARTHRITIS AND INCREASE IN CARTILAGE FORMATION

Embodiments of the present invention provide treatments for osteoarthritis (OA) and methods to increase production of cartilage in patients. By selectively absorbing or cushioning and redirecting pressure away from the affected joint or compartment, the wedged slab 12 and insole 22 facilitate proliferation of cartilage aggregates, which lead to increased cartilage production.

A hallmark of osteoarthritis (OA) is the progressive deterioration of joint cartilage. The degree of loss of articular cartilage (the area of the joint where the ends of the bones meet) has previously been classified. Table 1 provides the Outerbridge pathological classification system:

TABLE 1

Outerbridge pathological classification system

| Grade | Characteristics |
|---|---|
| 0 | Normal |
| I | Cartilage with softening and swelling |
| II | Partial-thickness defect with fissures on the surface that do not reach subchondral bone (the bone underneath the white joint cartilage) or exceed 1.5 cm in diameter |
| III | Fissuring to the level of subchondral bone in an area with a diameter more than 1.5 cm |
| IV | Exposed subchondral bone |

The Outerbridge IV lesion is characterized by the absence of cartilage and presence of exposed bone on the surface of the joint. When whole sections of Outerbridge IV lesions are harvested following total knee surgery and placed in tissue culture absent any opposing physical forces on the surface, the cartilaginous aggregates on or just below the surface survive. These aggregates are one potential source of cartilage regeneration when forces are reduced on that joint surface. This realization came about as a result of the current treatment for Outerbridge IV lesions; when knee joint cartilage is lost, it results in an abnormal angulation of the limb at the knee. This condition can result in bow leg (when the inner knee compartment loses its cartilage) or knock knee (when the outer compartment loses its cartilage). To rectify the condition, a bone cutting operation is performed to straighten the leg.[7]

Subsequent reports on this surgical procedure included inspection of the degenerative joint both before and after the operation. It was observed that areas completely denuded of articular cartilage had subsequent regrowth of cartilage following the operation. The hone cutting operation unloaded the forces across the affected compartment of the knee joint, allowing the cartilage to regrow.[8,9]

A similar result has been reported in connection with patients undergoing total hip replacement. The operation spontaneously unloaded the "other" or non-replaced arthritic hip following surgery on the opposite side. Though the patients had submitted to a total hip replacement on one side with plans for the other side to be treated within a few months, the patients subsequently refused the planned follow-up surgery as the previously "bad" hip was no longer troublesome. Following the surgeries, both patients were followed (for 7 and 11 years respectively). In both patients, the previously arthritic (non-replaced) hip, which had previously displayed bone/bone contact, grew a new joint space.[10] The significance of this report is that the unloading was spontaneous and probably intermittent and of minimal amount. Thereby indicating that minimal reduction in loads may have a potential for repair of even severe osteoarthritis. These conclusions are also consistent with studies showing that in some patients decreasing mechanical forces on degenerated joint surfaces stimulates formation of new biologic articular surface.[11]

The basis for this repair mechanism is known. The reduction in pressure probably allows the cartilaginous aggregates normally found on the Outerbridge IV lesions to proliferate and regenerate the previously damaged joint surface.[12]

A more in-depth study on the cartilaginous aggregates has also been reported. The aggregates were seen to histologically possess many of the properties of normal cartilage. For example, histochemical staining showed type II collagen and the lubricin molecule on the surface similar to normal articular cartilage. Lubricin is a water soluble glycoprotein encoded by the PRG4 gene. It has a molecular weight of 206 kD and consists of approximately equal proportions of protein and glycosaminoglycans. Also displayed was cellular-orientated architecture of both fibrocartilage and articular cartilage.[13] Further evidence of such repair phenomena has been reported in the hip by Milgram.[14]

It is clear from the medical literature that reduction of the abnormally high forces across the most severe arthritic joint can result in repair of the joint by regrowth of articular cartilage. The healing process is probably based upon the proliferation of the cartilaginous aggregates present on the surface of joints showing even the most severe arthritic condition.

The cushioned wedged insoles 22 and chambered insoles are demonstrated to cushion and selectively reduce load on weight-hearing joints. However, traditional heal wedges are shown not be effective. Accordingly, by using cushioned wedged insoles 22, wedged slabs 12 or chambered insoles a patient suffering from a medical condition such as OA may selectively reduce peak load on the affected joint or compartment and thus permit the proliferation of cartilage aggregates, which in turn leads to increased cartilage production. Specifically, a patient suffering from OA that is found to have decreased cartilage along the inner knee (medial compartment) may use the lateral wedges, which selectively reduces load from the medial compartment. If a patient suffering from OA is found to have decreased cartilage along the outer knee (lateral compartment), a medial wedge may be desired, which selectively reduces load from the lateral compartment. If the patient requires treatment of both the inner and outer compartment, the patient may periodically use the lateral wedge and medial wedge, which would selectively increase cartilage within the inner compartment and outer compartment. Thus the potential for repair exists.

Figure 17:
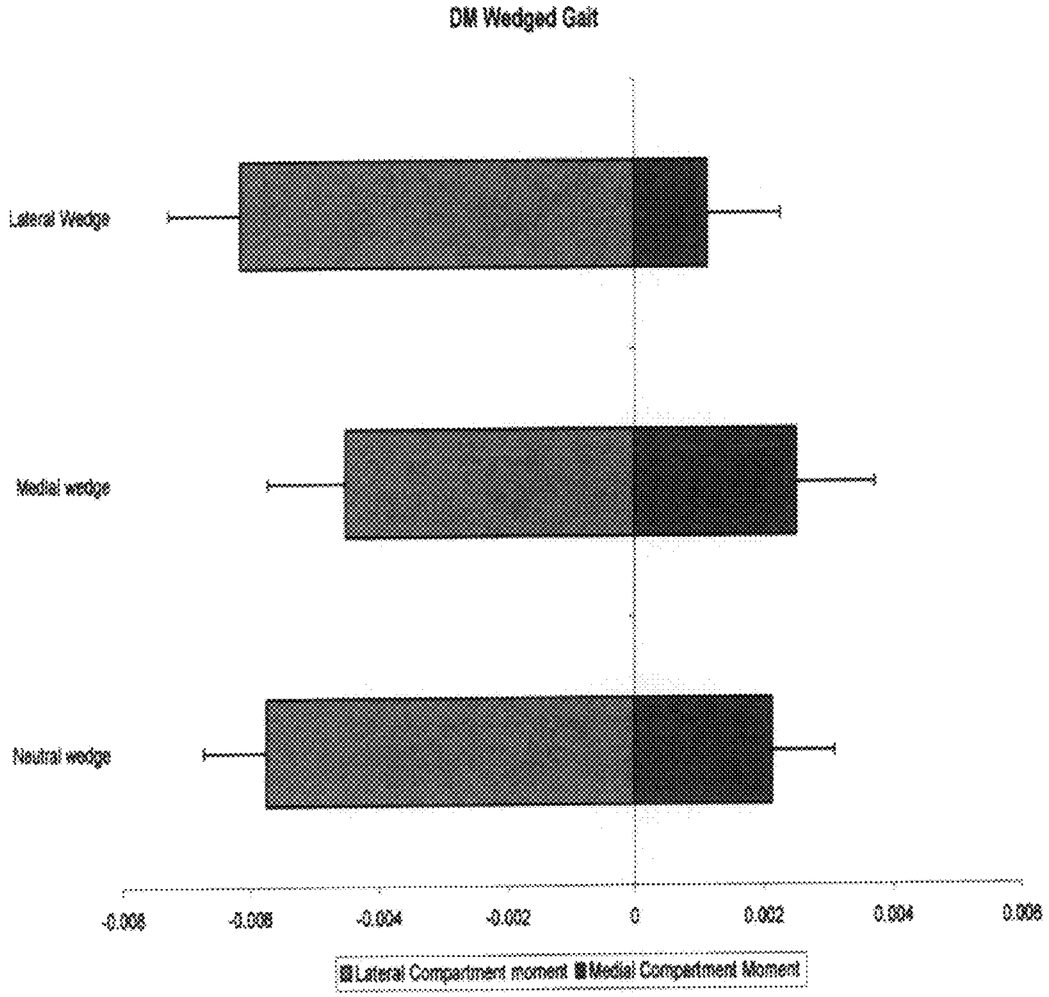
FIG. 17 is a bar graph depicting peak mediolateral forces exerted during gate of a subject three years after undergoing instrumented total knee replacement. The subject has an 11 degree valgus deformity, which replicates degenerative arthritis in the outer (lateral) compartment of the knee and collapse. Lateral wedge and medial wedged were each 2.5 degree wedges. Neutral wedge had no wedged configuration.

A demonstration of the applicability of cushioned wedged insoles 22 for the treatment of arthritic joints is demonstrated in FIG. 17. Specifically, a subject having a total knee replacement for three years was tested for mediolateral forces during gait when using either a 2.5 lateral wedge, a 2.5 medial wedge or a neutral wedged insole (no wedge). The subject had an 11 degree vulgus deformity, which replicates a patient having degenerative arthritis in the outer (lateral) compartment of the knee and collapse. As can be seen in FIG. 17, the 2.5 degree medial wedge provided 50% improvement in the unloading of the affected lateral compartment. The lateral wedge decreased the medial forces.

Figure 18:
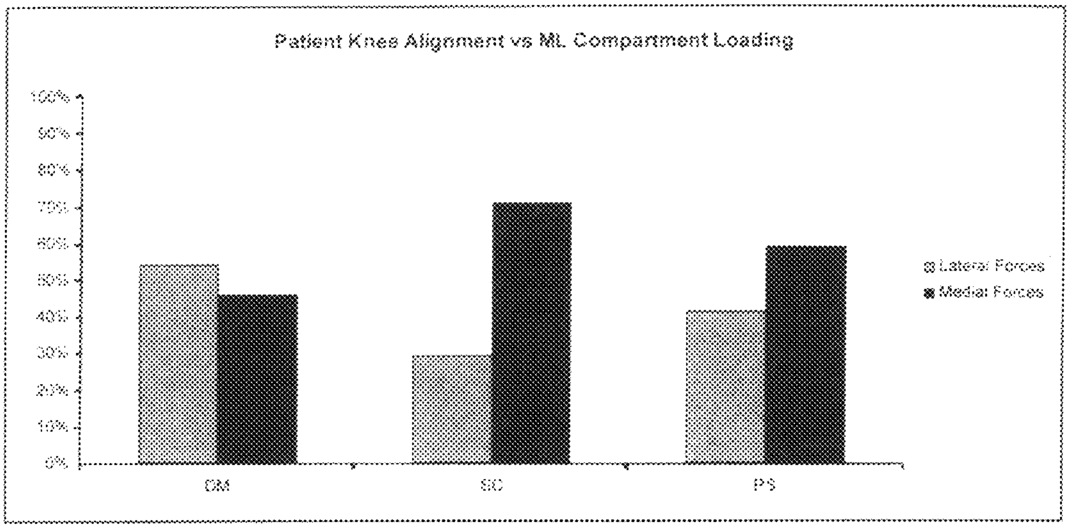
FIG. 18 provides a chart and bar graph showing knee alignment in comparison to peak mediolateral forces (both lateral and medial). The subjects include those with an 11 degree vulgus with 15 degree flexion contracture (DM), a 5 degree flexion contracture (SC), and a 5 degree varus (PS).

FIG. 18 demonstrates various mediolateral forces compared to various knee alignments. An 11 degree vulgus with 15 degree flexion contracture demonstrates increased forces on the lateral compartment and would thus be treated with a medial wedged insole. A 5 degree varus demonstrates increased forces on the medial compartment, which would be reflective of degenerative arthritis affecting the medial compartment and would therefore be treated with a lateral wedged insole. A 5 degree flexion contracture provides a significant increase in medial forces and would therefore be treated with a medial wedge.

While the cushioned wedged insoles 22 and slabs 12 may be used to treat osteoarthritis alone, a combined therapy may further enhance treatment. Thus, the cushioned wedged insoles 22 and slabs 12 may combined with pharmaceutical treatments to increase production of cartilage aggregates or cartilage in affected joints. A variety of treatments for osteoarthritis have been proposed, which typically involve injection into the affected joint itself In some embodiments cushioned wedged insoles 22 or slabs 12 are combined with the administration of a corticosteroid. In some embodiments the cushioned wedged insole 22 is combined with the administration of hyaluronic acid or a hyaluronic acid derivative. In some embodiments the cushioned wedged insoles 22 or slabs 12 are combined with HAYALGAN or SYNVISC.

G. METHODS OF TREATING ANKLE INJURIES USING A WEDGED INSOLE OR WEDGED SLAB

While the cushioned wedged insoles 22 have been show to prevent or treat sports injuries and medical conditions associated with weight-bearing joints, the methods also include treatments for a sprained ankle. Methods and devices for the treatment of a sprained ankle include use of a medial wedge or lateral wedge to cushion and to selectively reduce forces from the sprained region or chamber of the ankle.

The most common "sprain" occurs with the ankle rolling the foot inward, called an inversion injury (inversion is the movement of the foot sole towards the median plane or medial plane). This injures the ligaments on the outside, or lateral, side of the ankle. The opposite mechanism is an "eversion" injury where the sole of the foot moves away from the median plane, occurring at the subtalar joint. This injures the ligaments on the inner side of the ankle. However, severe sprains can result in injury to both sides of the ankle. The most severe type of this injury, called a high ankle sprain, can damage tissue higher up the leg and take much longer to heal.

By providing a cushioned wedged insole 22 or cushioned wedged slab 12, ankle sprains from both inversion and eversion may be treated. For example, in instances where an inversion force may tear the lateral ligaments the use of the cushioned lateral wedged insole could be used to restrict the inversion while keeping the tension off the previously damaged lateral ligaments. The methods include providing the cushioned wedged insole 22 to selectively relieve pressure from the inner or outer ankle depending on the patient's needs. Pressure relief is accomplished by both absorbing forces or cushioning from impact and by redirected forces away from the sprained site. Specifically, the lateral wedge relieves forces from the inner ankle or medial compartment and the medial wedge relieves forces from the outer ankle or lateral compartment. Further, periodic use or interchanging use of the lateral wedge and medial wedge may be desired in some instances.

H. USE OF WEDGED SLABS IN THE TREATMENT OR PREVENTION OF FOOT INJURIES

Cushioned wedged slabs 12 and cushioned wedged insoles 22 may also be used for treatment of tendon injury of the foot. Injuries of the foot commonly involve tendon injuries, and fractures, such as a fracture of the $5^{th}$ metatarsal. Cushioned wedged slabs 12 and cushioned wedged insoles 22 may be used to provide cushioning and to redirect forces away from the affected tendon or site of fracture. For instance a cushioned wedged slab 12 or insole 22 may redirect forces away from a fracture and provide cushioning in a fracture of the $5^{th}$ metatarsal using a medial wedged insole.

Although primarily discussed as a cushioned insole, one skilled in the art will now recognize, in some embodiments the customizable wedged slab 12 can also be cut to provide increased heel cushion, an arch support or a cushioned metatarsal pad. A non-limiting demonstration of shaping a universal cushioned wedged slab is shown as FIG. 6.

Isolated heel pain, often due to a bone heel spur or inflammation in the soft tissues under the heel, is a common human condition. A typical treatment involves the use of a cushioning insole that also elevates the heel, providing cushioning and shifting the force applied to the heel forward (toward the ball of the foot) at heel strike. In certain embodiments, the customizable cushioned wedged slab 12 can be cut across its width to accommodate the person's foot anatomy and shoe geometry to affect such a benefit.

Cushioned wedged slabs 12 can also be used for arch support. Fallen arch and high arch are common ailments related to abnormal foot anatomy. In either case, an arch support is often used to alleviate the condition. The customizable cushioned wedged slab 12 or cushioned neutral balance insole 32 can be formed for such a remedy. Specifically, the cushioned wedged slab 12 can be cut to the shape and size of the person's foot for correction. For example, the person can moisten the sole of the foot and stand on a section of water absorbent cardboard to visualize the exact anatomy of the foot. This pattern allows the person to determine the optimal location for one or more sections to be cut from the customizable cushioned wedged slab 12 to construct the height and width of the desired arch support, such as depicted in FIG. 6.

Cushioned wedged slabs 12 can also be used to treat pain or tenderness of the metatarsals (the 5 long bones of the foot). Treatment can be performed by applying a pad inside the shoe just behind the metatarsal heads to shift the force of the foot strike rearward into the non-tender soft tissues of the arch. Embodiments of the present invention can be adapted for treatment of the metatarsals by moistening the sole of the foot and standing on water absorbent cardboard to visualize the exact anatomy of the foot. This pattern allows the person to determine where to place the metatarsal pad. Sections can be cut from the customizable cushioned wedged slab 12 to construct the length and width of the metatarsal pad. In certain embodiments the higher portion 14 of the universal wedged slab 12 forms the distal portion of the orthotic.

The description provided herein, including the presentation of specific thicknesses, materials, and properties of the insole components, is provided for purposes of illustration only and not of limitation, and that the invention is limited only be the appended claims.

All headings are for the convenience of the reader and should not be used to limit the meaning of the text that follows the heading, unless so specified. Various changes and departures can be made to the present invention without departing from the spirit and scope thereof. Accordingly, it is not intended that the invention be limited to that specifically described in the specification or as illustrated in the drawings, but only as set forth in the claims. Although the invention has been described and illustrated with respect to exemplary embodiments thereof, it should be understood by those skilled in the art that the foregoing and various other changes, omissions, and additions can be made therein and thereto, without parting from the spirit and scope of the present invention.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. However, those of skill in the art should, in light of the present disclosure, appreciate that many changes can be made in the specific embodiments that are disclosed and still obtain a like or similar result without departing from the spirit and scope of the invention.

Example 1

Construction and Compression Test of EVA Wedged Insoles

Wedge insoles were tested for compression properties with a HFG-45 hand-held force gauge [(CE) Transducer Techniques, Temecula, Calif.] to ensure they retained a wedged configuration even during compression A 5-degree (relative to the bottom of the insole, measured from the thicker side to the thinner side) cushioned wedge insole was prepared from EVA. The thicker side of the insole measured about 12 mm in height, while the thinner side of the insole measured 4 mm. Under a force of 25-26 ft-lb (foot-pound) the 12 mm thick side reached maximum compression (to 5 mm). The 4 mm thick side reached maximum compression (to 1 mm) under a compression force of 20-26 ft-lb. As such, the EVA wedged insole was able to retain is generally wedged configuration during compression.

A 2.5-degree (measured from the thicker side to the thinner side) cushioned wedged insole was prepared from EVA. The thicker side of the insole measured about 8 mm in height, while the thinner side of the insole measured 4 mm. Under a force of 24-30 ft-lb the 8 mm thick side reached maximum compression (to 1 mm). The 4 mm thick side reached maximum compression (to 1 mm) under a compression force of 20-26 ft-lb. Thus, increased force was required to compress the thicker side.

The results suggest the 5 degree wedged insole may be preferred; however, the 2.5 degree wedged insole may also provide benefit over neutral insoles.

Example 2

Physical Properties of PORON Neutral Balance Insoles in Comparison to Cushioned Wedge Insoles Testing of the PORON material in a 4 mm-thick neutral balance insole was performed as follows. Maximal compaction of the 4 mm height is 1 mm. The force to maximal compaction is 9-14 ft-lb. Thus, in the neutral balance insole (of PORON), compaction stops at 1 mm depth. This endpoint is achieved by manually applying force of 9-14 ft-lb to an unconstrained insole.

In contrast, EVA cushioned wedged insoles force to compaction varied with the depth of the material. The 5 degree slope on its highest edge required more force to compaction than lesser depths of the same material. This material testing to maximum compaction is relevant as it is correlated with E-knee direct evidence results.

Example 3

Cushioned Wedged Insoles Shift Forces across the Medial Compartment of the Knee

Testing at the Shiley Center for Orthopedic Research and Education (La Jolla, Calif.) on patients with pressure sensing total knee replacement implants demonstrated the various peak mechanical forces across the knee during participation in various activities. When standing, the force across the knee joint is 3.5 times the body weight. When walking, force across the knee is 2.5 times the body weight at foot strike. These forces were also measured during a variety of sports, including golf. When a 75 year old swings a golf club at 65 miles per hour (relatively slow speed), the force on the back knee reaches 3.5 times body weight at impact while the force on the front knee reaches 4.5 times body weight.

The peak forces on the knee were measured compared to unloader braces (OSSUR) and wedged insoles, both lateral wedges and medial wedges. No change in forces was measured when using the unloader brace. Both lateral wedges and medial wedges demonstrated in the same subjects, 50% shifting of peak forces across the medial compartment of the knee, which was measured in inch moment. Thus, only the cushioned wedged insoles were effective at shifting the forces across the knee in this experimental in vivo model.

Example 4

Effect of the Don Joy Unloader Brace and Cushioned Wedged Insole on Knee Forces During the Golf Swing The Shiley Center for Orthopedic Research and Education (S.C.O.R.E.) at the Scripps Institute in La Jolla Calif. performed research on four patients with an experimental total knee implant called the "electronic" or "E-knee."

An 80 year old man with a right E-knee was tested to measure the effect of the wedge insole on the various knee forces generated by a golf swing. The subject was right handed and had an average swing speed of 65 mph. He had an 11 degree valgus and a 15 degree flexion contracture following the total knee replacement procedure. The subject had passive medial lateral laxity, but no drawer.

In testing, the collected data indicated that the Don Joy unloader brace set at 3 degrees had no effect on the peak knee forces measured during this subject's golf swing. This confirmed prior testing with the Don Joy unloader brace set on 2 other subjects (Bledsoe braces set at 5 degrees). In contrast, the EVA wedged insole to the medial (inner) side of the shoe specific for golf decreased the peak vertical loads on the lateral compartment 15-20% at hack swing, impact on the ball, and on follow through, as compared to forces generated without their use. Results of these tests are shown in the mediolateral force (×BW="times body weight") distribution graph seen in FIG. 8. Medial wedges progressively decrease peak lateral compartment loading during the impact and follow-though phases of the golf swing as compared to non-wedged insoles ("normal shoe neutral"). The cushioned wedges did not cause any significant changes in peak mediolateral loading during the takeaway phase of a golf swing.

Prior testing showed that the cushioned wedge insoles can unload the medial or lateral compartment up to 50% while walking, which imparts a lesser load on the back leg than the golf swing (2.5×body weight as compared to 3.25×body weight). Hitting from the rough increases peak loads across the knee and the wedge insoles showed their greatest reduction of peak loads when hitting a ball from this type of surface (see FIG. 9).

Further testing was performed at a golf course to assess real world conditions or applicability. The subject was a man with a slightly knocked knee joint alignment following his E-Knee replacement (this replicated the condition of arthritis on the outer side of the right or back leg of the right handed golf swing).

Tests were performed with and without spiked shoes. Surprisingly, spikes reduced the peak load compared to soft soled tennis shoes. It was thought the fixation to the ground with spikes would have prevented dispersion of the loads, but the evidence was to the contrary. The explanation was not readily apparent except there may be micromotion of the multiple pronged spikes to dissipate force.

Tests were performed to compare hitting off of fairway level grass with a wedge compared to hitting out of the rough. It was found that hitting from the rough resulted in decreased total vertical loads across the knee. However, at impact the joint experienced higher focused loads across the lateral compartment. This was thought to be due to the greater resistance of the club head going through the tall grass prior to hitting the ball buried in such. It is also possible this player may have stayed back on his right leg at impact.

Figure 8:
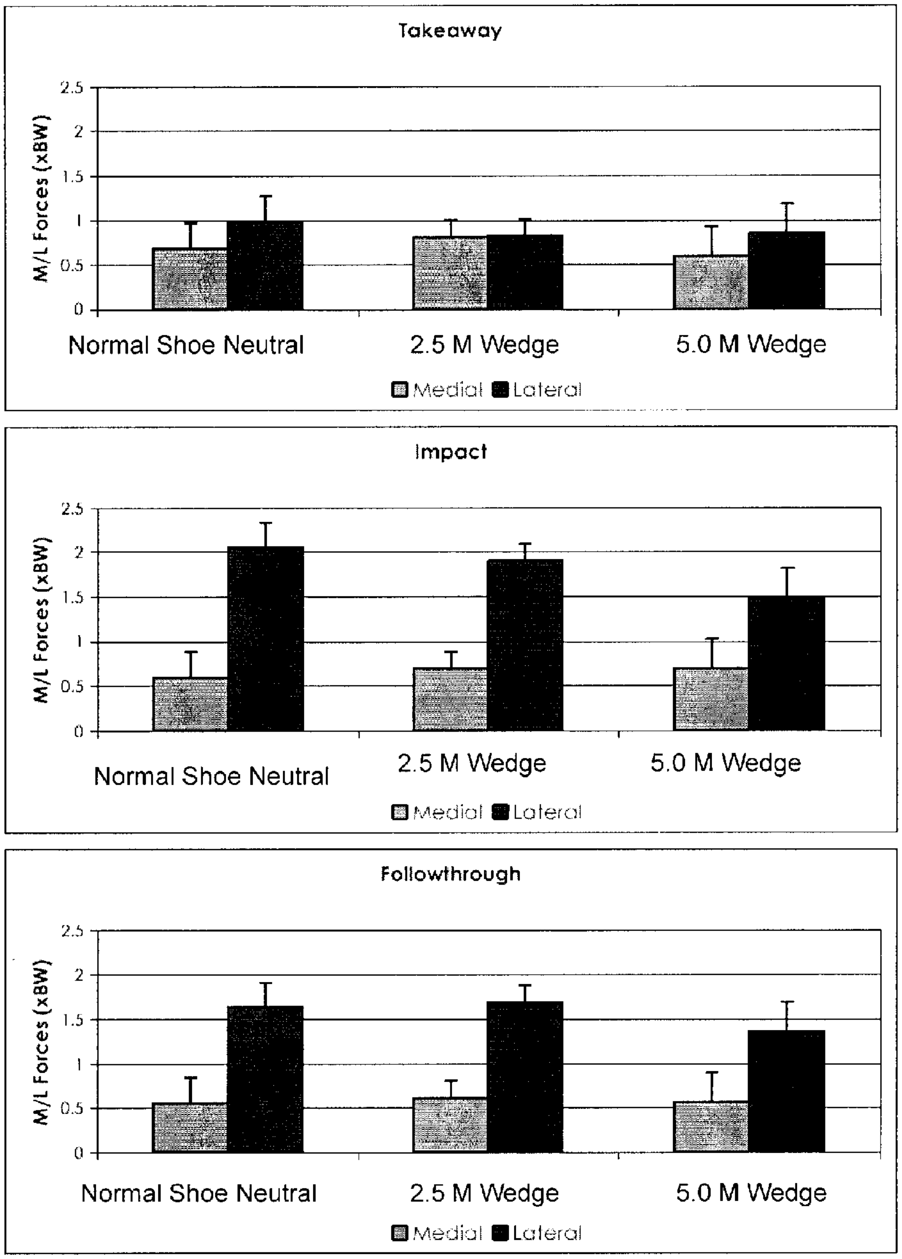
FIG. 8 is bar graph depicting a comparison of peak forces generated during a golf swing on both the medial compartment of the knee and lateral compartment of the knee during takeaway, impact and follow-through. “Normal shoe neutral” indicates no wedge, while “2.5 M Wedge” and “5.0 M Wedge” indicate a 2.5 degree medial wedge and 5.0 degree medial wedge respectively.
Figure 9C:
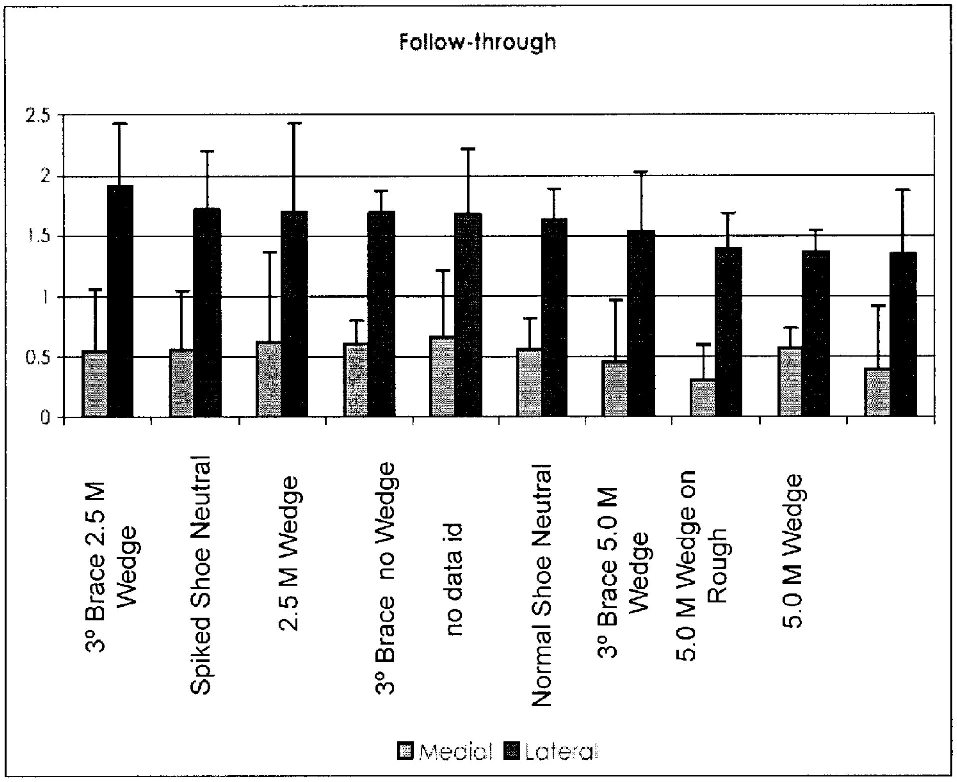

Various methods were explored to reduce the peak forces across the knee joint during the golf swing, with exemplary results shown in FIGS. 8 and 9. The most effective way to reduce the peak loads across the knee joint was the use of the cushioned wedged insole. The cushioned wedged insole was effective in reducing the total forces across the knee and specifically the lateral compartment loads. The insertion of the cushioned wedged insole reduced the total forces off fairway on the right or back knee by 15-20% and by an average of 25% when hitting out of the rough.

There was minimal difference in unloading the back knee's lateral compartment as compared with an "unloader" brace at the 3 degree setting. However, there was a 56% load decrease on the lateral compartment at impact when the brace and the 5 degree sloped EVA insole were used in combination.

Direct measurement of peak knee joint loads with the electronic knee showed the loads to be surprisingly high even at slow club head speeds. It is anticipated that higher swing speeds, such as those achieved by stronger golfers, will cause greater loads.

FIGS. 8 and 9 show the changes in mediolateral force distribution caused by various devices during three phases of a golf swing. The 5 degree medial wedged insole showed the greatest decrease in lateral compartment loading. During the takeaway phase of a golf swing, the 3 degree brace and spiked shoes show an increase in lateral compartment loading, while 2.5 degree and 5 degree medial wedges showed a decrease in lateral compartment loading. In the impact phase, the greatest lateral forces occur while wearing normal shoes without wedges. The lateral forces during impact are decreased with both 2.5 degree and 5 degree wedges. During follow-through, 3 degree brace and spiked shoes show the greatest lateral compartment loading.

In summary, the 2.5 degree and 5 degree wedges effectively reduced peak loads on the lateral compartment. At impact, the wedges performed similarly, except that for cases where the ball was hit from the rough, the 5 degree slope had most benefit. On follow through, the lateral compartment of the back knee had similar results.

Example 5

Effect of Foot Positioning and Cushioned Wedged Insoles on Mediolateral Force Distribution During the Golf Swing FIG. 10 is a bar graph showing the changes in peak axial force on the forward (left) leg caused by various devices during the impact phase of a golf swing at impact. The bottom bar is the control bar, meaning there were no insoles utilized, only the golf shoe with soft spikes.

From top to bottom, the chart shows the following compared to the controls which are similar in medial/lateral loading at impact.

The 5° MedWedge (45° turnout) lessened the medial compartment peak load as compared to the control. For this data, the golfer wore a 5° medial wedge and turned his left foot 45° toward the target (as opposed to positioning the foot parallel with the right foot).

The 5° MedWedge (parallel) minimally lessened medial load. For this data, the golfer wore a 5° medial wedge and positioned the left foot parallel with the right foot.

The 5° LatWedge (45° turnout) lessened medial compartment load. For this data, the golfer wore a 5° lateral wedge and turned his left foot 45° toward the target.

The 5° LatWedge parallel also lessened medial load. For this data, the golfer wore a 5° lateral wedge and positioned the left foot parallel with the right foot.

The 2.5° LatWedge 45° turnout also lessened medial load as compared to the control. For this data, the golfer wore a 2.5° lateral wedge (and turned his left foot 45° toward the target).

The 2.5° LatWedge parallel lessened medial load; however load was reduced less drastically than with the 5 degree lateral wedge. For this data, the golfer wore a 2.5° lateral wedge and positioned the left foot parallel with the right foot.

The 2.5° MedWedge 45° turnout minimally lessened medial load. For this data, the golfer wore a 2.5° medial wedge and turned his left foot 45° toward the target.

The 2.5° MedWedge parallel minimally lessened medial load. For this data, the golfer wore a 2.5° medial wedge and positioned the left foot parallel with the right foot.

Control 45 turnout—for this data, the golfer wore only soft spiked golf shoes and turned his left foot 45° toward the target.

Control parallel feet—for this data, the golfer wore only soft spiked golf shoes and positioned the left foot parallel with the right foot.

The greatest reduction in the medial compartment peak force at impact on the left knee was found to be when the golfer turned the left foot out 45° and wore a 2.5° sloped lateral wedged insole; however, each of the lateral wedges appear successful.

Example 6

Reduction of Medial Forces During Gait Using Cushioned Wedged Insoles

A barefoot (stocking feet) test subject was used to evaluate the effect of the wedge insoles on medial compartment forces. FIG. 11A shows the results of the testing. The center bar is the control, which included walking barefoot in stocking feet. Either lateral or medial wedged insoles were placed inside the stockings as no shoes were worn. The laterally placed wedged insoles of 2.5 and 5.0 degree slopes showed the greatest reduction in peak forces in the medial compartment in the knee. Medial wedges did not appear to unload the medial compartment and 5 degree medial wedges significantly increased load in the medial compartment.

FIG. 11B demonstrates the effect of cushioned wedges on gait when wearing conventional shoes. As with the barefoot study, peak medial forces were found to decrease the greatest when using lateral wedges with 5 degree slope.

These tests also predict that a restricted subtalar (below the ankle) motion will dampen the effect of the cushioned wedge insoles. The reason appears to be that the foot and ankle must first respond to the altered force at foot impact to create a relative flat (piano valgus) foot position. It is known that people with this foot position tend to have "knocked knee" which in effect reduces the forces across the medial joint. That result is exactly what is intended with the lateral elevation of the wedged insole placed laterally in the shoe.

Example 7

Figure 13:
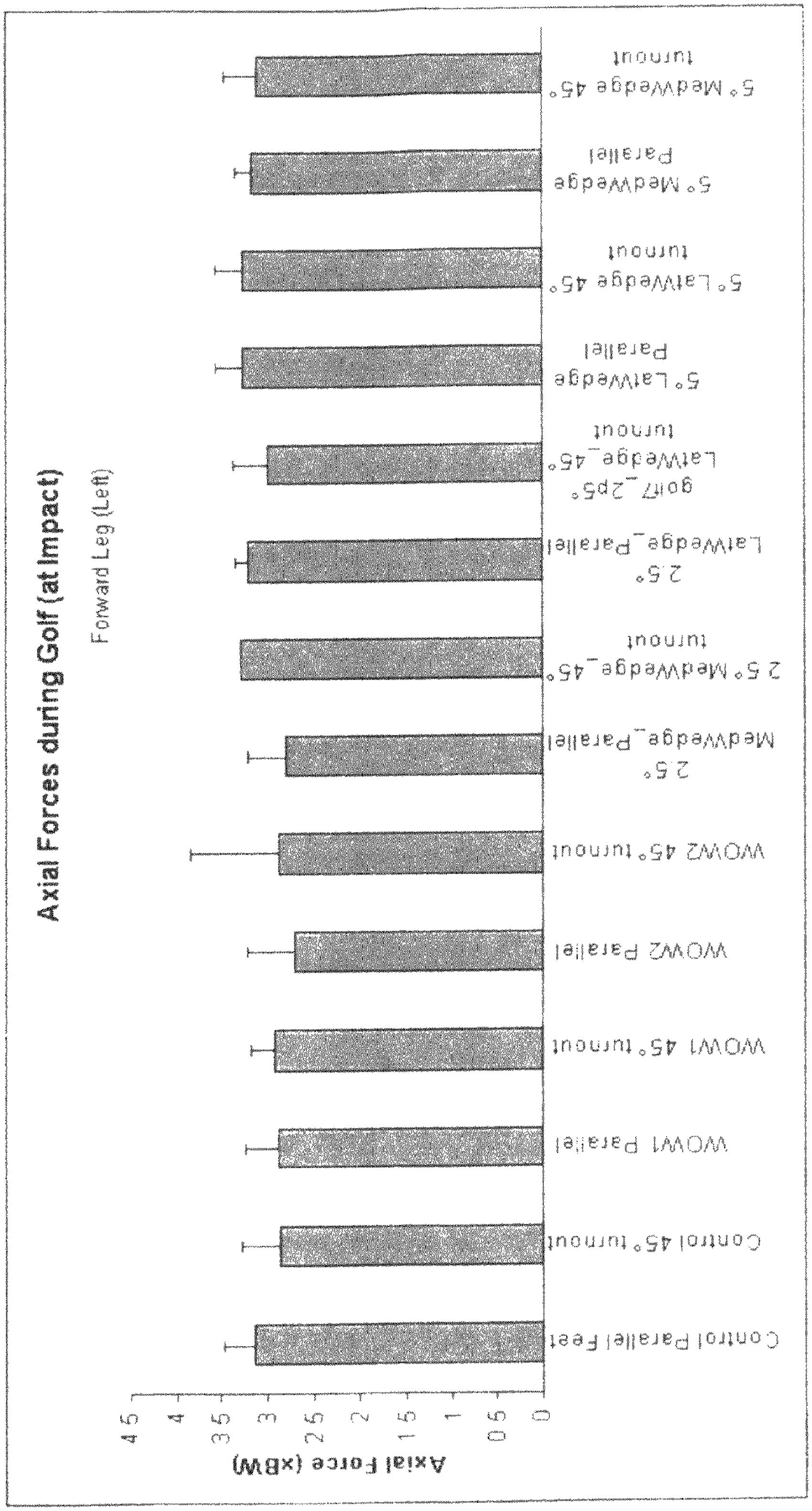
FIG. 13 is a bar graph depicting the effects of foot positioning (with or without wedged insoles) on peak axial forces upon the knee at golf ball impact. Data is shown for the forward (left) leg of a right-handed golfer. "Turnout" refers to positioning the left foot to point approximately 45° toward the target rather than "Parallel," in which the foot is positioned parallel to the right foot. "MedWedge" refers to use of a medial wedge. "LatWedge" refers to use of a lateral wedge. The "2.5°" and "5°" refer to the slope of the wedged insole. The "Control" bars refer to forces generated without the use of any insole.
Figure 14:
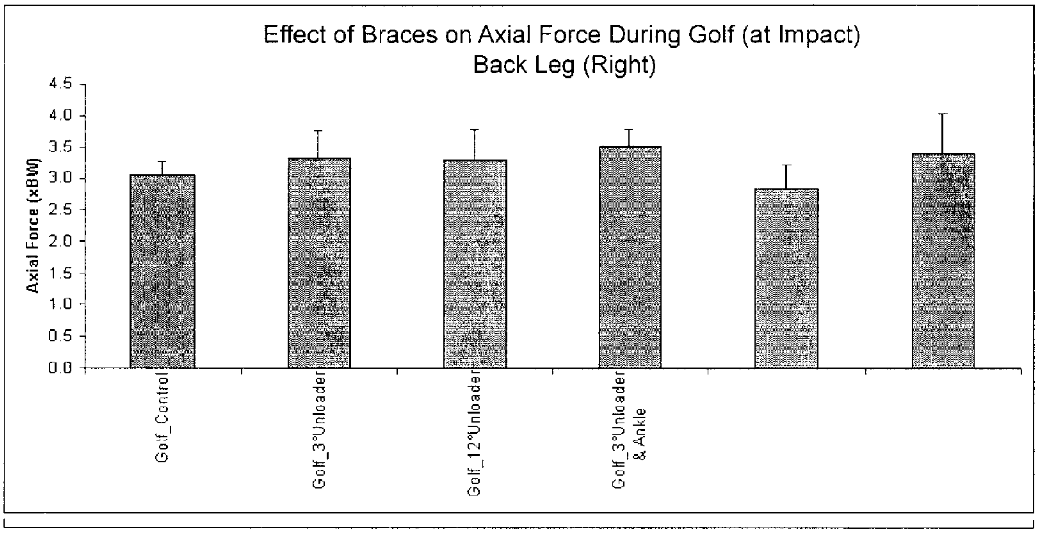
FIG. 14 is a bar graph depicting the inability of unloader braces to reduce peak axial forces on the right (back) knee during the golf swing at impact.

Comparison of Axial Forces At Impact of the Golf Swing Using Cushioned Insoles Peak axial forces during the golf swing were measured at impact using the E-knee as referenced above and compared by body weight. Specifically, in this study peak axial forces on the forward leg are displayed in FIG. 13 and peak forces on the back leg are displayed in FIG. 14. Traditional unloader braces seemed ineffective whether provided at 3° or 12°. Cushioned wedges appeared to have less change in total axial force in the front leg; however, forces present could have been effectively shifted between lateral and medial compartments.

Example 8

Traditional Gel Insole Sorbothane does not Reduce Axial Loads or Significantly Affect Mediolateral Forces Peak axial loads of a variety of insoles were assessed for their ability to reduce peak axial loads. Compared to barefoot only Canadian military insole was found to significantly reduce peak axial loads. Surprisingly, Sorbothane, which is a soft open cell cushion found in many shoes, was not effective at reducing peak axial loads. The 5° lateral wedge showed slightly better unloading than barefoot. Results are show in FIG. 15A.

Figure 15B:
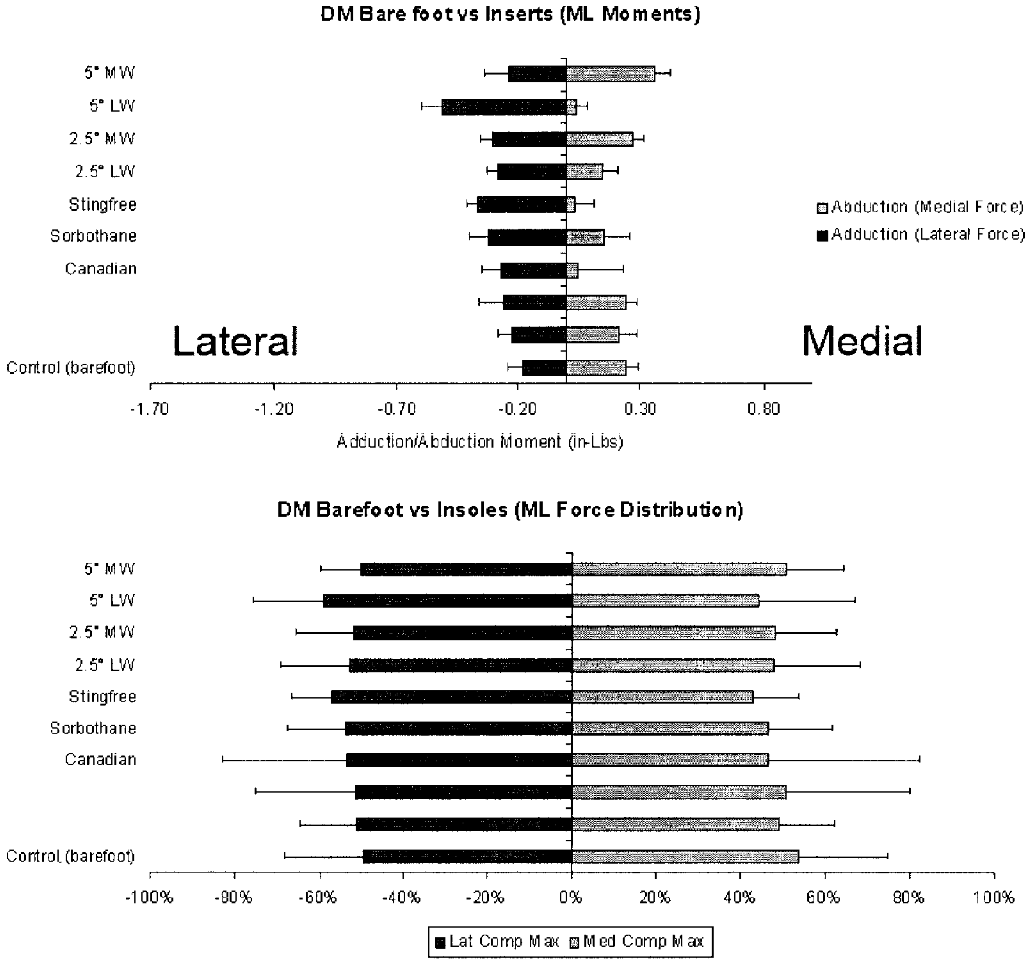
FIG. 15B is a bar graph depicting peak forces on the lateral compartment and medial compartment of the knee joint using a total knee implant with load sensors.
Figure 16:
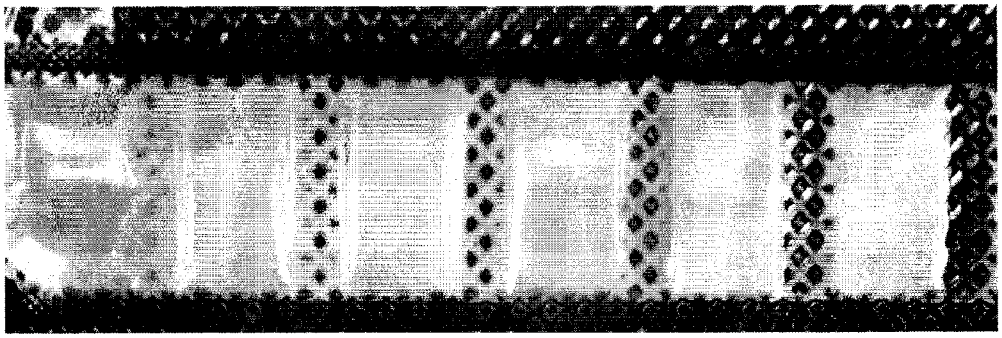
FIG. 16 is a photograph of a chambered insole layer for insertion of hetereogenous materials including a heterogeneous mixture of rigid and soft materials to mimic human anatomy for insoles.

Mediolateral transfer of forces were measured using the E-knee as described above. Canadian military insole and 5° lateral wedge showed the most significant transfer of load from the medial compartment to the lateral compartment. Results are shown in FIG. 15B.

Example 9

Identification of Cartilage Aggregates in Outerbridge IV Lesions

In degenerative arthritis the Outerbridge IV lesion is considered an end-stage lesion. The potential for a natural articular surface repair has been reported. However, an in-depth pathological study has not been available. The purpose of this study was to examine the gross and microscopic characteristics that can serve as the foundation for cartilage repair.

Human osteochondral specimens harvested following total knee surgery were subjected to visual examination before and after Safranin O (which selectively stains the aggregates and adjacent intact cartilage) staining. Correlative histology was performed.

The stained gross specimens showed cartilaginous aggregates on the surface as well as multiple small depressions. The microscopy showed cartilaginous aggregates on the surface staining positive for glycosaminoglycans, type II collagen, and lubricin. The depressions or pits were due to three conditions: aggregate erosion, vascular rupture, and bone fragmentation.

The cartilaginous aggregates have potential for proliferation contributing to cartilage repair. The multiple small pits could be the home for various cell therapies (e.g., synovial or stem cells) or other therapeutics.

Example 10

In Vitro Growth of Cartilage Aggregates in Outerbridge IV Lesions

Cartilage aggregates found in Outerbridge IV lesions have the potential to grow and generate repair tissue. Full-thickness loss of articular cartilage (Outerbridge IV lesion) can have potential for repair given the proper environment. Regrowth of cartilage has been reported following unilateral total hip arthroplasty when the unoperated hip was protected by shifting weight-bearing to the asymptomatic operated side. There are also reports of cartilage formation following valgus-producing high tibial osteotomy. The purpose of this study was to validate the potential for the cartilage aggregate to be the source of such a repair. The hypothesis was that these aggregates grow and contribute to local cartilage repair when the contact forces are removed.

Osteochondral specimens from Outerbridge IV lesions were harvested from patients undergoing total knee surgery. Multiple disc-shaped samples were prepared for tissue culture. The specimens were stained (without fixing) with Safranin O. This technique quantitated the size of the cartilage aggregates in live specimens and permitted monitoring of potential growth in culture as well as subsequent histology.

Absent any surface pressure, motion, and synovial fluid found in vivo, the cartilage aggregates showed no repair over the surface of the exposed hone in tissue culture. Histologic examination at 3 and 6 weeks revealed maintained viability of the aggregates covering the surface.

The cartilage aggregates did not proliferate in tissue culture but remained viable, supporting the speculation that they are contributors to the cartilage repair following reduction in joint pressure in vivo on such a lesion.

REFERENCES

1) Martin Lotz, Noboru Taniguchi, Beatriz Carames, Ulrich Ulmer, Lorenza Ronfani, Marco E. Bianchi. Setsuro Komiya; Aging-related loss of chromatin protein HMGB2 in articular cartilage is linked to reduced cellularity and osteoarthritis. Proceedings of the National Academy of Sciences (published online Jan. 12, 2009); available at http://www.pnas.org/content/early/2009/01/12/0806062106.abstract.
2) Ledingham J, Regan M. Jones A, Doherty M; Radiographic patterns and associations of osteoarthritis of the knee in patients referred to hospital. Annals of Rheumatic Disease 1993, 52:520-526.
3) Guccione A A, Felson D T, Anderson J J, Anthony J M, Zhang Y, Wilson P W F, Kelly-Hayes M, Wolf P A, Kreger B E, Kannel W B; The effects of specific medical conditions on the functional limitations of elders in the Framingham study. American Journal of Public Health 1994, 84:351-358.
4) Dieppe P, Brandt K D; What is important in treating osteoarthritis? Whom should we treat and how should we treat them? Rheum. Dis. Clin. N. Am. 2003, 29(4):687-716.
5) Dieppe P A. Ebrahim S, Martin R M, Juni P: Lessons from the withdrawal of rofecoxib. Bmj 2004, 329(7471):867-868.
6) Wang Y, Simpson J A, Wluka A E, Teichtahl A J, English D R, Giles G G, Graves S, Cicuttini F M; Relationship between body adiposity measures and risk of primary knee and hip replacement for osteoarthritis: a prospective cohort study. Arthritis Research & Therapy 2009, 11:R31 (Mar. 5, 2009).
7) Coventry M B; Upper Tibial Osteotomy for Degenerative Arthritis. J. Bone Joint. Surg. 1985, 67A; 1136-1140.
8) Koshino T, Wada S, Ara Y, Saito T; Regeneration of degenerated articular cartilage after high tibial valgus osteotomy for medial compartment osteoarthritis of the knee. Knee 2003; 10(3):229-36.
9) Kanamiya, T, Naito, M, Hara, M, Yoshimura, I; The influences of biomechanical factors on cartilage regeneration after high tibial osteotomy for knees with medial compartment osteoarthritis. Arthroscopy: The Journal of Arthroscopic & Related Surgery, Volume 18, Issue 7, 725-729.
10) Guyton G P, Brand R A; Apparent spontaneous joint restoration in hip osteoarthritis. Clin. Ortho. Rel. Res. 2002, No. 404, 302-307.

11) Buckwalter J A, Martin J A, Brown T D, Perspectives on chondrocytes and Rehabilitation, Biotechnology 2006; 43(3-4):603-9

12) Johnson, L L; Arthroscopic Surgery; Principles and Practice. C. V. Mosby. St. Louis, Mo. USA. 1986

13) Zhang D, Johnson L L, Hsu H P; Spector M. Cartilaginous deposits in subchondral bone in regions of exposed bone in osteoarthritis of the human knee: Histomorphometric study of PRG4 distribution in osteoarthritic cartilage Journal of Orthopaedic Research Volume 25, Issue 7, 873-883.

14) Milgram J W; Morphologic alterations of the subchondral bone in advanced degenerative arthritis. Clin. Orthop. 1983 173:293-312.

What is claimed is:

1. A method of treating osteoarthritis in a subject suffering from an arthritic joint, comprising:

providing a cushioned wedged slab comprising a flat bottom and a sloping top that defines a lower edge and an upper edge that extend parallel and longitudinally along the entire slab, wherein the wedged slab is constructed from a material that partially collapses under compressive force and rebounds when the compressive force is removed;

determining whether the subject suffers from arthritis of a medial compartment or a lateral compartment;

tailoring a lateral wedged insole from the wedged slab to reduce force on a medial joint compartment if the subject suffers from arthritis of a medial compartment, or tailoring a medial wedged insole from the wedged slab to reduce force on a lateral joint compartment if the subject suffers from arthritis of a lateral compartment;

wherein the step of tailoring the lateral or medial wedged insole comprises placing an insole template on the bottom or top of the wedged slab depending on (a) whether the subject suffers from arthritis of the lateral compartment or the medial compartment, and (b) the location of the arthritic joint, and trimming the wedged slab to match the template; and treating the subject with the tailored wedged insole, wherein the subject wears the thickest side of the wedged insole below the lateral side of the subject's foot if suffering from arthritis of a medial compartment, or the subject wears the thickest side of the wedged insole below the medial side of the subject's foot if suffering from arthritis of a lateral compartment.

2. The method according to claim 1, further comprising administering an injection of corticosteroid medication into the arthritic joint.

3. The method according to claim 2, further comprising administering injections of a hyaluronic acid derivative into the arthritic joint.

4. The method of claim 3, wherein the hyaluronic acid derivative comprises HYALGAN or SYNVISC.

5. The method according to claim 1, further comprising wearing a knee unloader brace.

6. The method according to claim 1, wherein said material is EVA foam.

7. The method according to claim 1, wherein a lateral wedged insole is characterized by the upper edge positioned along an outer length of the insole and the lower edge towards an inner length of the insole.

8. The method according to claim 1, wherein a medial wedged insole is characterized by the upper edge positioned along an inner length of the insole and the lower edged towards the outer length of the insole.

9. The method according to claim 1, wherein a thickness of the upper edge measures between 7 millimeters and 14 millimeters and a thickness of the lower edge measures about 4 millimeters, further wherein the wedge comprises a slope from 2.5 degrees to 5 degrees.

10. The method according to claim 1, wherein the lateral wedged insole is worn to increase cartilage aggregates in a medial joint compartment and the medial wedged insole is worn to increase cartilage aggregates in a lateral joint compartment.

11. The method according to claim 1, wherein the medial wedged insole and lateral wedged insole are periodically worn to increase cartilage within either the medial or lateral joint compartment.

* * * * *